US009006393B1

(12) United States Patent
Clark et al.

(10) Patent No.: US 9,006,393 B1
(45) Date of Patent: Apr. 14, 2015

(54) MOLECULAR CONSTRUCTS AND USES THEREOF IN RIBOSOMAL TRANSLATIONAL EVENTS

(76) Inventors: Patricia L. Clark, South Bend, IN (US); Michael S. Evans, South Bend, IN (US); Krastyu G. Ugrinov, Notre Dame, IN (US); Thomas Clarke, IV, Notre Dame, IN (US); Marc-André Frese, Enger (DE)

( * ) Notice: Subject to any disclaimer, the term of this patent is extended or adjusted under 35 U.S.C. 154(b) by 1214 days.

(21) Appl. No.: 11/211,723

(22) Filed: Aug. 26, 2005

Related U.S. Application Data

(60) Provisional application No. 60/604,459, filed on Aug. 26, 2004.

(51) Int. Cl.
*A61K 38/04* (2006.01)
*C12N 15/00* (2006.01)
*C40B 30/04* (2006.01)

(52) U.S. Cl.
CPC ...................................... *C40B 30/04* (2013.01)

(58) Field of Classification Search
None
See application file for complete search history.

(56) References Cited

U.S. PATENT DOCUMENTS 6,620,587 B1    9/2003    Taussig et al.

OTHER PUBLICATIONS

Parry, Nature, 413, 848-852, 2001.*
Nakatogawa et al., Cell, 108, 629-636, 2002.*
Hochuli et al., Bio/Technology 1988, 1321-1325.*
Fang, P., et al., "A nascent polypeptide domain that can regulate translation elongation," PNAS, 2004, pp. 4059-4064 v. 101 No. 12, The National Academy of Sciences of the USA.
Lovett, Paul S., et al., "Ribosome Regulation by the Nascent Peptide," Microbiological Reviews, 1996, pp. 366-385 v. 60 No. 2, American Society for Microbiology.
Morris, David R., et al., "Upstream Open Reading Frames as Regulators of mRNA Translation," Molecular and Cellular Biology, 2000, pp. 8635-8642 v. 20 No. 23, American Society for Microbiology.
Speed, M.A., et al., "Conformation of P22 tailspike folding and aggregation intermediates probed by monoclonal antibodies," Protein Sci., 1997, pp. 99-108, Cold Spring Harbor Laboratory Pres.
Adams, S.R. et al. "New Biarsenical Ligands and Tetracysteine Motifs for Protein Labeling in Vitro and in Vivo: Synthesis and Biological Applications" *J Am. Chem. Soc.*, 124 (2002), pp. 6063-6076.
Berisio, R. et al. "Structural Insight Into the Role of the Ribosomal Tunnel in Cellular Regulation" *Nat. Struc. Biol.*, 10 (2003), pp. 366-370.
Clark, P.L. "Protein Folding in the Cell: Reshaping the Folding Funnel" *Trends Biochem Sci.*, 29, (2004) pp. 527-534.

Clark, et aL "A Newly Synthesized, Ribosome-Bound Polypeptide Chain Adopts Conformations Dissimilar from Early in Vitro Refolding Intermediates" *J Biol. Chem*, 276, (2001) pp. 25411-25420.
Crameri, et al. "Improved Green Fluorescent Protein by Molecular Evolution Using DNA Shuffling" *Nat. Biotechnol.*, 14, (1996) pp. 315-319.
Dedmon, et al., "FlgM Gains Structure in Living Cells", *Proc. Natl. Acad. Sci. USA*, 99, (2002), pp. 12681-12684.
Fedorov, et al. "Process of Biosynthetic Protein Folding Determines the Rapid Formation of Native Structure" *J. Mol. Biol.*, 294, (1999), pp. 579-586.
Friguet, et al. "Properties of Monoclonal Antibodies Selected for Probing the Conformation of Wild Type and Mutant Forms of the P22 Tailspike Endorhamnosidase" *J Biol. Chem.*, 265, (1990), pp. 10347-10351.
Friguet, et al. "In Vitro and Ribosome-bound Folding Intermediates of P22 Tailspike Protein Detected with Monoclonal Antibodies" *J. Biol. Chem.*, 269, (1994), pp. 15945-15949.
Friguet,.et al. "Measurements of the True Affinity Constant in Solution of Antigen-Antibody Complexes by Enzyme-Linked Immunosorbent Assay" *J. Immonol. Methods*, 77 (1985), pp. 305-319.
Friguet, et al. "Polypeptide-Antibody Binding Mechanism: Conformational Adaptation Investigated by Equilibrium and Kinetic Analysis" *Res. Immunol*, 140, (1989), pp. 355-376.
Frydman, et al. "Co-Translational Domain Folding as the Structural Basis for the Rapid de novo Folding of Firefly Luciferase" *Nat. Struct. Biol.*, 6, (1999), pp. 697-705.
Fuchs, et al. "In Vitro Folding Pathway of Phase P22 Tailspike Protein", 30 (1991), pp. 3598-6604.
Ghaemmaghami, et al. "Quantitative Protein Stability Measurement in vivo" *Nat. Struct. Biol*, 8, (2001), pp. 879-882.
Griffin, et al. "Specific Covalent Labeling in Recombinant Protein Molecules Inside Live Cells" *Science*, 281, (1998), pp. 269-272.
Hanes, et al. "In Vitro Selection and Evolution of Functional Proteins by Using Ribosome Display" *Proc. Natl. Acad. Sci. USA*, 94, (1997), pp. 4937-4942.
Hanes, et al. "Stop Codons Preceded by Rare Arginine Codons Are Efficient Determinants of SsrA Tagging in *Escherichia Coli*", *Proc. Natl. ead. Sci.*, 99, (2002), pp. 3440-3445.
Ignatove, et al. "Monitoring Protein Stability and Aggregation in vivo by Real-Time Fluorescent Labeling" *Proc. Natl. Acad. Sci. USA*, 101 (2004), pp. 523-528.
Jain, et al. "Monoclonal Anitbody Epitope Mapping Describes Tailspike β-Helix Folding and Aggregation Intermediates", *J. Biol. Chem.*, 280, (2005), pp. 22032-23040.

(Continued)

Primary Examiner — Nancy T Vogel
(74) Attorney, Agent, or Firm — Denise L. Mayfield; Husch Blackwell LLP

(57) ABSTRACT

Stalled ribosome:nascent molecule of interest complexes and methods of using same are provided. Plasmids, particularly DNA plasmids, comprising a stall segment are also disclosed. The methods provide for the facile and stable formation of stalled ribosome:nascent molecule of interest complexes that may be used to examine protein synthesis and protein conformational events, as well as in the creation of desired ribosomal displays. Cells transformed with these plasmids are also provided, and include both eukaryotic and prokaryotic transformed cells. Stall elements that provide for ribosomal stalling of eukaryotic and prokaryotic ribosomes are also disclosed. Various therapeutic and clinical applications of these methods are also provided and used in diseases associated with defects in protein accumulation in vivo.

17 Claims, 6 Drawing Sheets

(56) References Cited

OTHER PUBLICATIONS

Janzen, et al. "Inhibition of Translation Termination Mediated by an Interaction of Eukaryotic Release Factor 1 with a Nascent Peptidyl-tRNA", *Molecular and Cellular Biology*, 22, (2002), pp. 8562-8570.

Keppetipola, et al. "Rapid Detection of in Vitro Expressed Proteins Using Lumio™ Technology", 25.3 (2003), pp. 7-11.

King, et al. "Thermolabile Folding Intermediates: Inclusion Body Precursors and Chaperonin Substrates" *Faseb J.*, 10 (1996), pp. 57-66.

Komar, et at "Cotranslational Folding of Globin" *J. Biol. Chem.*, 272 (1997), pp. 10646-10651.

Laemmli, U.K. "Cleavage of Structural Proteins During the Assembly of the Head of Bacteriophage T4" *Nature*, 227 (1970), pp. 680-685.

Malkin, et al. "Partial Resistance of Nascent Polypeptide Chains to Proteotytic Digestion Due to Ribosomal Shielding" *J. Mol. Biol.*, 26 (1967), pp. 329-346.

Mitraki, et al. "Global Suppression of Protein Folding Defects and Inclusion Body Formation" *Science*, 253 (1991). pp. 54-58.

Nakatogawa, et al. "The Ribosomal Exit Tunnel Functions as a Discriminating Gate" *Cell*, 108 (2002), pp. 629-636.

Nicola, et al. "Co-Translational Folding of an Alphavirus Capsid Protein in the Cytosol of Living Cells" *Nat. Cell. Biol.*, 1 (1999), pp. 341-345.

Nissen, et al. "The Structural Basis of Ribosome Activity in Peptide Bond Synthesis" *Science*, 289 (2000), pp. 920-930.

Ominato, et al. "Identification of a Short Highly Conserved Amino Acid Sequence as the Functional Region Required for Post-transcriptional Autoregulation of the Systathionine γ-Synthase Gene in *Arabidopsis*" *J. Biol. Chem.*, 277(39), (2002), pp. 36380-36386.

Onouchi, et al. "Nascent Peptide-Mediated Translation Elongation Arrest Coupled with mRNA Degradation in the CGS1 Gene of *Arabidopsis*" *Genes & Development*, 19, (2005), pp. 1799-1810.

Spedding, G. "Isolation and Analysis of Ribosomes from Prokaryotes, Eukaryotes, and Organelles" *Ribosomes and Protein Synthesis*, (1990), Oxford University Press, New York, pp. 1-27.

Steinbacher, et al. "Phage P22 Tailspike Protein: Crystal Structure of the Head-Binding Domain at 2.3 Å, Fully Refined Structure of the Endorhamnosidase at 1.56 Å Resolution, and the Molecular Basis of O-Antigen Recognition and Cleavage", *J. Mol. Biol.*, 267, (1997), pp. 865-880.

Steinbacher, at at " Crystal Structure of P22 Tailspike Protein: Interdigitated Subunits in a Thermostable Trimer" *Science*, 265 (1994), pp. 383-386.

Sunohara, et al. "Ribosome Stalling During Translation Elongation Induces Cleavage of mRNA Being Translated in *Escherichia coli*" *J. Biol. Chem.*, 279, (2004), pp. 15368-15375.

Woolhead, et al. "Nascent Membrane and Secretory Proteins Differ in FRET-Detected Folding Far Inside the Ribosome and in Their Exposure to Ribosomal Proteins" *Cell*, 116, (2004), pp. 725-736.

\* cited by examiner

TAILSPIKE MONOMER
CCPGCC MOTIF INCORPORATION SITE

Y556

K229 mAb 236 BINDING EPITOPE

CCPGCC MOTIF INCORPORATION SITE

β-HELIX DOMAIN

N-TERMINAL DOMAIN

MOLECULAR CONSTRUCTS AND USES THEREOF IN RIBOSOMAL TRANSLATIONAL EVENTS

CROSS-REFERENCE TO RELATED APPLICATIONS

This application claims the benefit of U.S. provisional application No. 60/604,459 filed Aug. 26, 2004, which is hereby incorporated by reference herein.

GOVERNMENT INTEREST STATEMENT

The United States Government owns rights in the present invention as research relevant to the development of the invention was supported by United States federal funds from the National Science Foundation, Contract/Grant Number MCB-0237945.

SEQUENCE LISTING

The instant application contains a Sequence Listing which has been submitted in ASCII format via EFS-Web and is hereby incorporated by reference in its entirety. Said ASCII copy, created on Sep. 2, 2011, is named 34341420.txt and is 10,868 bytes in size.

BACKGROUND

1. Field of the Invention

The present invention relates generally to the field of genetic molecular tools, particularly those molecular tools that may directly or indirectly direct translation and the activity of ribosomes. The invention also relates to the field of pharmacologically active molecule screening methods, as genetic molecular tools are provided that are used in a variety of screening methods.

2. Related Art

Co-translational protein folding and maturation are often studied in cell-free translation mixtures, using stalled ribosome-nascent chain complexes produced by translating truncated mRNA. This approach has at least two important limitations: (i) it can be technically challenging, and (ii) it only works in vitro, where the concentrations of cellular components are different from concentrations in vivo.

Newly synthesized polypeptide chains first pass through the ribosomal exit tunnel, which spans ~100 Å between the peptidyl transferase site and the surface of the ribosome[1,2] (FIG. 1A). The tunnel protects 30-40 aa of the nascent chain from contact with other cellular components, and restricts the accessible conformational space[3,4]. As the nascent chain lengthens, its N-terminus emerges into the cytosol. At this point, the chain has access to additional conformational space, and may also interact with other cellular components.

The rate of nascent chain synthesis (~20 aa/sec in E. coli) is considerably slower than many folding events, some of which occur on a microsecond timescale. The difference between these rates implies that protein folding can begin during chain synthesis, and co-translational folding has been detected experimentally[5-9]. Co-translational folding therefore represents a fundamentally different starting ensemble for folding than dilution of a full length chain out of a chemical denaturant[10], and conformations populated by nascent chains in vivo can be populated quite differently (or not at all) during refolding in vitro[6,9]. For a given protein, co-translational folding might therefore modify the dominant folding pathway, potentially influencing aggregation propensity. Yet, while recent studies have made some progress in tracking and observing the folding of proteins within intact cells[11-13], the earliest steps of folding in vivo (while chain synthesis is underway) remain unclear, in part because of a lack of tractable methods to dissect these early folding steps.

Translation mixtures (and intact cells) include ribosomes bearing nascent chains of all lengths. This heterogeneity means there currently are no biophysical techniques available to assess nascent chain conformation as translation occurs. Uncoupling chain elongation and folding, typically by increasing the population of ribosomes bearing nascent chains of a discrete length, can, however, provide 'snapshots' of nascent chain conformations during synthesis.

Producing stalled ribosomes bearing nascent chains of a uniform length remains a substantial technical hurdle for measuring ribosome-bound nascent chain conformations. Current methods to create stalled E. coli ribosome-nascent chain complexes are technically quite challenging, particularly for longer nascent chain lengths.

The above and other limitations in the art associated with ribosome-nascent chain manipulation currently limit the efficiency and potential powerful applications for using ribosomes in various biophysical analytical techniques, including ribosome display. A need continues to exist in the art for more reliable and reproducible techniques for capturing and monitoring translational events involved in the genesis of proteins, as well as protein conformation events related thereto.

SUMMARY

The present invention is directed to overcoming the above-mentioned and other challenges related to the use of ribosomes and molecular constructs that may be created and analyzed using them in examining protein synthesis in vitro and in vivo.

The present invention is exemplified in a number of implementations and applications, some of which are summarized below.

In some aspects, a stall element suitable for use in a molecular construct with a ribosome is provided. The stall element when used as part of the constructs and methods described herein will cause translation to stall at an amino acid (such as the C-terminal proline (P) residue, the "stall" point) in or near the sequence when inserted into a gene of interest.

In some embodiments, the stall element is described as comprising a stall sequence having a structure as defined in Formula I:

F-X1-WI-X2-GIRAGP           (SEQ ID NO: 1)

wherein X1, X2, or both X1 and X2 comprise 1 or more amino acid residue. In some embodiments, X1 comprises 1 to 4 amino acid residues. In some embodiments, X2 comprises 1 to 4 amino acid residues. In other embodiments, X1 is an amino acid sequence other than the sequence STPV (SEQ ID NO: 2) where X2 is a sequence SQAQ (SEQ ID NO: 3). In other embodiments, X2 is other than a sequence SQAQ (SEQ ID NO: 3) where X1 is STPV (SEQ ID NO: 2). In some embodiments, the stall element comprises a sequence of 17 or more amino acid residues.

In other embodiments, the stall element comprises a molecular tag. In some embodiments, the molecular tag is a histidine tag, or a cMyc-tag or a FLAG-tag for antibody binding, for example. In some of these embodiments, the tag is a histidine tag, and the histidine tag is embedded within the stall sequence. In some of these embodiments, X1 is 1 to 4 histidine residues where X2 is 1 to 3 histidine residues. In other embodiments, X1 is 1 to 3 histidine residues where X2 is 1 to 4 histidine residues. In other embodiments, both X1 and X2 are 1 to 3 histidine residues. In other embodiments, X2 is 1 to 4 histidine residues and X1 is a sequence other than 1 to 4 histidine residues. In other embodiments, the histidine tag comprises a sequence including histidine residues attached to the C-terminus of the stall element.

In a particular embodiment, X1 includes 1 to 3 histidine residues and X2 includes 1 to 4 histidine residues. In one such embodiment, the stall element comprises a sequence:
FXHHHWIHHHHGIRAGP (SEQ ID NO: 4), or
FHHHHWIHHHXGIRAGP (SEQ ID NO: 5),
wherein X is other than histidine.

The presence of histidine (H) residues within the stall element increases the affinity of the stall element for an affinity separation material, such as to a metal species on a separation column. Hence any molecule that is complexed or attached to the stall element may be isolated using standard affinity based separation techniques, such as via nickel affinity chromatography. In particular aspects, the presence of the histidine residues in the stall element facilitates recovery of any desired nascent chain of interest from a reaction mixture resulting from a stalled translation event.

In some embodiments, the histidine tag (His-tag) of the stall element is flanked on either end by one or more restriction endonuclease sites. In some embodiments, the His-tag is flanked (on each side) by one or more (such as five (5)) unique restriction sites. The restriction sites located on either side of the His-tag of some of the constructs described herein facilitate the insertion of the stall element (sequence) at any position of interest within a gene where translation stall is desired. For example, in some embodiments, it may be desirable to insert the stall element within a particular gene (or within a chromosome) or other desired sequence, structure or construct.

In some embodiments, the stall element is described as comprising a six (6) amino acid segment having an amino acid sequence modeled on a portion of a SecM sequence (GIRAGP) (SEQ ID NO: 6). However, any eukaryotic or prokaryotic amino acid sequence that is capable of stalling ribosome translation may be used in the model presented herein. Particular other stall elements may be modeled after eukaryotic sequences and elements, such as, for example, gp48, CPA 1, arg-2, CGS 1, and others. Suitable stall sequences include those that are capable of arresting or inhibiting the native rate of ribosomal translation relative to the rate of ribosomal translation in the absence of a stall element.

The stall sequences of the invention are characterized by the ability to induce permanent or transient translational arrest of a ribosome at a selected, discrete point on a nucleic acid sequence of interest. This feature permits the formation of large, easily detectable quantities of ribosome-associated nascent molecule chains of uniform and predictable size and length suitable for detailed biophysical analysis. In this regard, compositions enriched for a particular desired species of stalled ribosome:nascent molecule of interest complex are provided.

The stall element as described herein may be used in a variety of applications and incorporated into both recombinant (plasmid-borne) genes and chromosomal gene(s). Such applications may be used to knock down the expression of a particular gene, or to regulate the appearance of a protein in a cell or animal.

In some embodiments, the nascent molecule of interest may comprise a molecule such as a non-natural (e.g., polyglycine) or natural (polypeptide) chain (peptide, protein). The protein or peptide may have any desired length of amino acids, and in some embodiments may be described as a nascent chain having a length of from 1 to 900 or more amino acids. In some embodiments, the nascent molecule comprises a protein or peptide having an amino acid length of 15 to 800, 20 to 700, or 50 to 800 amino acid residues.

The stalled ribosome:nascent molecule of interest complexes are relatively stable, and remain intact for many hours. By way of example, the stalled ribosome:nascent molecule of interest constructs remain stable for at least 24 hours or more in vitro. Compositions that are enriched for particular species of stalled ribosome:nascent molecule complexes are more easily subject to detailed biophysical analysis of particular nascent chain molecules of interest, and are more easily purified from other cellular components, such as by, for example, standard sucrose gradient centrifugation techniques.

The length/size of the nascent molecule of interest as part of the complex may be manipulated to modulate the efficiency and/or detectability of a desired species of stalled ribosome:nascent chain complex. For example, in some embodiments, where the nascent molecule of interest comprises a relatively long length of amino acids (such as 800 or more amino acid residues), a generally lower detectable arrest will be observed. While not intending to be limited to any mechanism of action or theory, it may be that "drag" produced by a very long nascent chain acts to disrupt the stabilizing interactions between a stall sequence and the ribosome tunnel during translation.

Shorter nascent chains (such as 50 to 800 amino acid residues), as part of the described stalled ribosome:nascent molecule complex provide even more greatly improved stall efficiencies. An advantage of using this size range of nascent chain in vivo (in a cell) exists in that the presence of this size range of nascent chain molecules is not likely to be toxic to the cell. Furthermore, most nascent molecules of interest also tend to fall within this size range.

In some embodiments, 2% or more, or even up to 50%, 60% or more, of the entire cellular ribosomal pool may be present in the form of desired stalled ribosome:nascent chain complexes employing the herein disclosed methods and stall elements. Even shorter nascent chains (such as 15 to 40 amino acid residues in length) are effective at arresting translation using the herein described stall element and methods, again providing a steady state level of arrested ribosome:nascent chain complexes of about 2% or more, and up to 50% or more, of an entire cellular ribosomal pool.

In some embodiments, the stalled ribosome construct comprises a ribosome that is a eukaryotic, archaea or prokaryotic ribosome, such as an *E. coli* ribosome. Thus, in some embodiments, the constructs include stable ribosome:nascent molecule of interest (chain encoding a protein or peptide, or non-natural molecule such as polyglycine) complexes on ribosomes from any organism. It is envisioned that the presently described methods and constructs may be used in the study and characterization of protein maturational processes that are specific to any particular organism or class of organism. These processes include, by way of example, the translocation of nascent chains into the endoplasmic reticulum (ER), including covalent, post-translational modifications to a nascent molecule, such as to a polypeptide chain (for example, glycosylation).

In yet another aspect, a plasmid, such as a DNA plasmid, is provided. In some embodiments, the plasmid comprises a nucleic acid sequence encoding a nascent molecule of interest and a stall element as described herein. In some embodiments, the plasmid is a DNA plasmid. The DNA plasmid is also described as suitable for use in the transformation of a cell, so as to form a transformed cell. Translation by a ribosome of the nucleic acid sequence of the transformed cell will result in the stopping, or "stalling" of the ribosome at the "stall" point on or near a stall element. By way of example, a "stall" point in one embodiment of the stall element comprises a terminal proline (P) residue, as depicted in Formula I. The result of ribosomal stalling is the formation of stable arrested ribosome:nascent molecule of interest complexes. These complexes may be used in several different biophysical analytical methods useful in the identification and characterization of biologically and pharmacologically important molecules. Some of these applications are described herein.

In some embodiments, the DNA plasmid having a nucleic acid sequence comprising a stall element as described herein also comprises a molecular tag. For example, a molecular tag my comprise a histidine tag or embedded histidine residue and/or sequence of 1 or more histidine residues. An advantage of the featured histidine tags and residues in the construct is that they facilitate the recovery of nascent molecules of interest (chains).

In another embodiment, a plasmid, such as a DNA plasmid is provided that comprises a stall element as described herein, and 1 or more unique restriction endonuclease sites located on either side (i.e., flanking) said stall element. More specifically, in some embodiments, 1 or more of the restriction endonuclease sites are located at a position 5' of the stall element, and 1 or more of the restriction endonuclease sites are locate 3' of the stall element. In some embodiments, these restriction endonuclease sites facilitate the targeted insertion of a nascent molecule of interest at a position in front of (5') the stall element. In some embodiments, there are 2 unique restriction endonuclease sites located at a position 5' of the stall element, and 1 unique restriction endonuclease site located at a position 3' of the stall element. In some embodiments, the unique restriction endonuclease sites flanking the stall element are positioned in tight and/or in close proximity to the stall element.

In some embodiments, a DNA plasmid is provided that comprises a nascent chain of interest, a stall element and a C-terminal post-stall element. In some embodiments, the post-stall C-terminal element may comprise a degradation tag (such as a sequence, 'ANDENYALAA') (SEQ ID NO: 7) or an aggregation-prone sequence (such as a human light chain antibody sequence or a wild-type green fluorescent protein sequence). These C-terminal post-stall elements provide yet an additional advantage in that they reduce and/or eliminate the accumulation of released nascent chains that escape binding at the ribosome in a reaction environment (cell or extract), and thereby reduce background readings and increase the accuracy and efficiency of subsequent molecular analysis.

In another aspect, a method is provided comprising tracking and observing early translational events, simultaneously with ribosome translation of a nascent peptide or protein chain, in vitro or in vivo. In other aspects, a method is provided for tracking and observing co-translational multimerization (dimmers, etc.) of a nascent molecule/chain of interest.

In some embodiments, the methods employ the use of a stall element comprising a stall sequence of Formula I:

F-X1-WI-X2-GIRAGP (SEQ ID NO: 1), wherein X1, X2, or both X1 and X2 are 1 to 4 amino acid residues. In some embodiments, X1 of Formula I comprises an amino acid sequence STPV (SEQ ID NO: 2), X2 comprises an amino acid sequence SQAQ (SEQ ID NO: 3), or X1 comprises the amino acid sequence STPV (SEQ ID NO: 2) and X2 comprises the amino acid sequence SQAQ (SEQ ID NO: 3).

In some embodiments, the methods do not involve in vitro translation. In other embodiments, the methods do not employ truncated mRNAs. Furthermore, in some embodiments, the methods described herein employ mRNA species that posses a stop codon, unlike other techniques that employ truncated mRNA and/or mRNA lacking a stop codon. The molecular constructs employed in the presently described method, particularly the stall element and the stalled ribosome:nascent chain complex, enable a vastly improved approach for the analysis of translational events and for achieving targeted halting or stalling of translation in vivo. Another advantage of the constructs and methods described herein includes the ability to use them efficiently with both circular and linear DNA. The constructs and methods are advantageously suitable for use in translation halting or stalling both in vitro or in vivo (in a cell).

In yet another aspect, a method is provided comprising forming a stalled ribosome:nascent molecule, wherein the nascent molecule comprises a nascent chain (sequence) of interest having a uniform size and/or length. Stalled ribosome:nascent molecules may then be used in standard molecular analytical techniques known to those of skill in the art to provide information on protein/peptide genesis, folding, maturation and related molecular events. As part of the method, the stall element as defined in Formula I or II is used so as to provide a stall tag within the stalled ribosome:nascent molecule of interest. Such provides a powerful molecular tool having a variety of analytical and clinical applications.

In another aspect, a method of enhancing translational stalling in a cell is provided. For example, this may be provided by expressing the stalled construct as described herein in an *E. coli* strain deficient for an endogenous mechanism involved in translational events. By way of example, such may comprise an *E coli* cell strain that is lacking ssrA (also known as tmRNA). ssrA is the endogenous mechanism responsible for release of stalled ribosomes. One such deficient *E. coli* strain is CH113 (Hayes, C. S., et al., (2002)[43]).

In another aspect, a method is provided comprising providing a ribosomal display. In some embodiments, the method comprises preparing a tagged library of candidate mRNAs having a stall element from a DNA library. Then, translating the candidate tagged pool of mRNAs to provide a pool of stalled ribosome:mRNA complexes, the mRNAs encoding a library of nascent chains of interest. The pool of stalled ribosome:mRNA complexes may then be translated so as to yield a pool of ribosome:nacent chain complexes. In this manner, a ribosomal display of a desired nascent chain of interest (protein/peptide) is created. These translated complexes may then be screened with a selective agent having affinity for the nascent chain, so as to provide a selected pool of ribosome-bound nascent chains of interest.

Because the mRNA encoding the nascent chain of interest also includes a stall element (for example, a stall element of Formula I or Formula II as defined herein), these selected mRNA species may be efficiently processed to obtain the corresponding DNA product. This may be accomplished using a primer that binds specifically to the stall sequence. Using a standard reverse transcription polymerase chain reaction (RT-PCR), a pool of selected mRNAs, freed away from ribosome, may be processed to produce a corresponding pool of DNA. These DNA may then be sequenced for any desired further applications or study (e.g., sequence alignment analysis).

In yet another aspect, a method comprising transforming cells (in vivo) with a plasmid construct is provided. In some embodiments, the method comprises transforming cells with a DNA plasmid having a nascent chain of interest followed by a stall element (for example, a stall element as described in Formula I or II) to provide a pool of transformed cells having a tagged (stall segment) nascent molecule of interest. This pool of transformed cells may then be treated to induce expression of the nascent molecule of interest. From this, a pool of stalled ribosome:nascent molecule constructs within the cell may be provided.

In some embodiments of the method, the pool of transformed cells prepared as above may be lysed, and the pool of stalled ribosome:nascent molecule constructs selected, isolated, and the corresponding selected mRNA stall tagged sequences reverse transcribed to provide identifiable DNA sequences.

It is expected that the in vivo (cell) applications of the methods disclosed herein find particular applicability with nascent chain molecules having a length of from about 50 to about 800 amino acid residues. This size range of proteins/peptides is not particularly toxic to the cell, and permits a level of transcription in the cell sufficient for maintaining cell viability/survival.

In yet another aspect, a method comprising forming a ternary construct comprising an mRNA:ribosome:nascent molecule complex is provided. These ternary complexes are formed using the stall element having a Formula I:

F-X1-WI-X2-GIRAGP            (SEQ ID NO: 1), wherein X1, X2, or both X1 and X2 are 1 to 4 amino acid residues.

A library of these ternary constructs, for example a library containing mRNA corresponding to mutant protein sequences of interest, may then be screened (such as over a column of immobilized drug or other binding partner) to provide a screened pool of ternary complexes. The screened pool of ternary complexes may then be treated with an agent to destabilize the ternary structure (such as with EDTA), and to isolate mRNAs. The collected mRNAs may then be subject to subsequent amplification (such as by reverse transcription and PCR(RT-PCR)).

In yet another aspect, a eukaryotic stall element is provided. While many eukaryotic stall elements may be created and used according to the present invention, one embodiment of the eukaryotic stall element may be modeled after a CGS1 stall element. In some embodiments, the eukaryotic stall element comprises a stall sequence of Formula II:

X1-RR-X3-X2, wherein X1 comprises 1 or more histidine residues, 1 or more amino acid residues other than histidine, or a combination thereof, and where X2 comprises 1 or more histidine residues, one or more amino acid residues other than histidine, or a combination thereof, and wherein said stall element is capable of stalling translation of a eukaryotic ribosome. In some embodiments, X3 is other than a sequence NCSNIGVA (SEQ ID NO: 8). Methods using these eukaryotic stall elements are also provided. In some embodiments, X3 comprises 1 or more amino acid residues. In other embodiments, X3 is other than a sequence NCSNIGVA (SEQ ID NO: 8). In yet other embodiments, X3 comprises 1 or more histidine residues. Methods using these and other eukaryotic stall elements in the practice of the invention are also provided.

The following abbreviations are used through out the description of the present invention:
aa—amino acid
nt—nucleotide
mRNA—messenger RNA
tRNA—transfer RNA
NMR—nuclear magnetic resonance
uORF—upstream open reading frame
GFP—green fluorescent protein
DNA—deoxyribonucleic acid
RNA—ribonucleic acid The following conversion chart presents the one-letter designation and three letter designation of the amino acids species used in the description of the various stall element sequences and associated modifications thereof presented.

| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

The above summary of the present invention is not intended to describe each illustrated embodiment or every implementation of the present invention. The figures and the detailed description that follow more particularly describe these example embodiments.

BRIEF DESCRIPTION OF THE DRAWINGS

The invention may be more completely understood in consideration of the detailed description of various embodiments of the invention that follows in connection with the accompanying drawings, in which:

FIG. 1A-1C, in accordance with one embodiment of the invention, illustrates the design of stalled ribosome-nascent chain complexes using the SecM stall sequence. (1A) Nascent chain of interest (solid line) proceeds through the exit tunnel in the 50S subunit (back-slashed line area). Portions of the 17aa SecM stall sequence (solid circles) interact with components of the ribosomal exit tunnel, in particular, protein L22 (stippled line area), to induce translation stalling. The 30S subunit is indicated in the forward-slashed line area. (1B) The tailspike-SecM and GFP stall sequence fusions used in this study. Length represents the length from N-terminus to the SecM stall point; the sum of tailspike or GFP residues, Glu and Arg from the SacI restriction site linker, and the 17 aa of the SecM stall sequence, FSTPVWISQAQGIRAGP (SEQ ID NO: 9). A star indicates the point of translation stalling, corresponding to the final Pro of the stall sequence, which remains at the peptidyl transferase center of the 50S subunit[14]. (1C) Ribbon diagram of the native tailspike homotrimer[32]. One tailspike monomer chain is indicated by the stippled line. The indicated amino acids correspond to the locations of each SecM stall sequence insertion. For fluorescence studies, the CCPGCC (SEQ ID NO: 10) FlAsH binding site motif[20], was incorporated in the Nterminal domain of tailspike, replacing residues 102-107. For C-GFP49, the CCPGCC (SEQ ID NO: 10) motif was incorporated at the extreme N-terminus of the polypeptide. The approximate location of the mAb 236 binding epitope[17] is indicated by the circle.

Reference will now be made in detail to the exemplary embodiments of the invention, examples of which are illustrated in the accompanying drawings. Wherever possible, the same reference numbers will be used throughout the drawings to refer to the same or like parts.

DETAILED DESCRIPTION

Figures 1A, 1B:
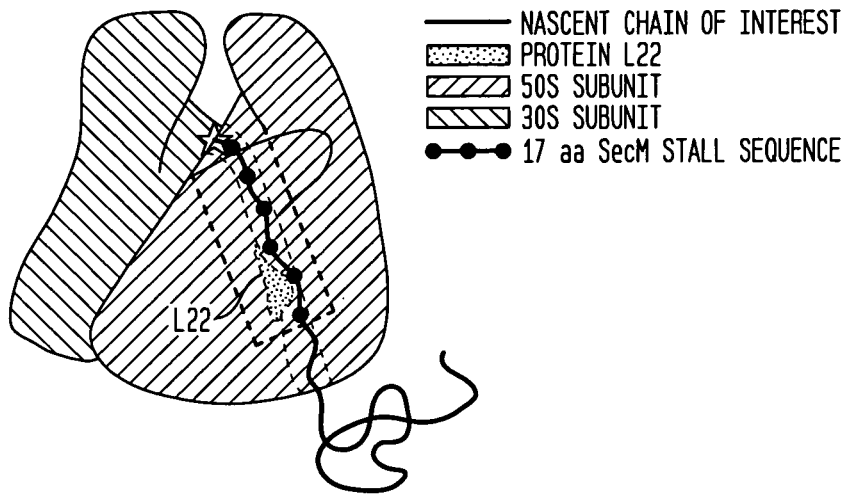

The present invention provides stable molecular constructs and methods for tracking and inhibiting protein synthesis and selection through the manipulation of ribosome activity. These constructs and methods provide for the efficient and stable formation of large amounts of stable ribosome:nascent molecule constructs. These constructs are characterized in some embodiments as comprising uniform sizes/lengths of nascent molecules, such as protein and/or peptide chains of relatively the same length.

The constructs described herein are useful in a variety of different types of biophysical measurements, such as NMR, that require large quantities and concentrations of stalled ribosome-nascent chain complexes. These large samples would be technically impossible or prohibitively expensive to produce using traditional ribosome stalling methods based on in vitro translation of truncated mRNAs. The stall element described herein, such as a stall element modeled after a portion of the SecM stall sequence, provides a directed method that facilitates the production of large quantities of stalled ribosome-nascent chain complexes. The method may be used with conventional E. coli, or other types of cultures, to yield rapid results with high efficiency.

A particular advantage of the constructs and methods includes their amenability to analysis in both in vivo and in vitro systems. In particular, the utility of the constructs/methods in vivo enable the analysis of a wide range of nascent chain conformation and interaction studies, including chain length- and sequence-dependent binding of molecular chaperones and/or membrane targeting processes.

The constructs presented include nascent chain molecules having any desired length, and produce stalled ribosome-associated nascent chain complexes that accumulate to levels well within the detection limits of the assays presented. In addition, comparable stall efficiencies were observed with constructs that contained nascent chains differing at least ten-fold in length between the longest (TFS) and shortest (C-GFP49) nascent chains. This demonstrates yet another advantage of the stall element directed techniques described herein over previously available approaches, as a more robust method suitable for studying a wide range of sizes of virtually any nascent molecule of interest.

Using some embodiments of the constructs, a much higher percentage of stable stalled ribosomes may be produced in vivo compared to the number obtained using the same stall construct in vitro. For example, with constructs having a nascent molecule structure/length similar to TβS, the stall element directed stalling produces a much higher percentage of stalled ribosomes in vivo than in vitro (52% versus 23%). While in vitro translation lysates contain all factors necessary for translation, they are nevertheless more dilute and lack the complexity of the cellular environment. The altered translation environment might explain the less efficient and more equivalent stalling that will be observed for some nascent molecules of interest, such as those similar to the three tailspike nascent chain constructs examined here in vitro.

DEFINITIONS

Where the definition of terms departs from the commonly used meaning of the term, applicant intends to utilize the definitions provided herein, unless specifically indicated otherwise.

It should be noted that the singular forms, "a", "an" and "the" include reference to the plural unless the context as herein presented clearly indicates otherwise.

"Stall element" relates to an element comprising a stall sequence.

A "stall sequence" relates to a nucleic acid sequence or an amino acid sequence, of eukaryotic and/or prokaryotic origin, that is capable of disrupting, inhibiting or reducing the translational activity of a ribosome (eukaryotic or prokaryotic).

"Nascent molecule" relates to a non-natural (e.g., polyglycine) or natural (e.g., peptide, protein) molecule, or a fusion product or combination of a natural molecule and a non-natural molecule. The peptide or protein may comprise a fusion protein or peptide. The protein or peptide may also be described as a eukaryotic or prokaryotic protein or peptide, or a hybrid molecule thereof. The nascent molecule may comprise a nucleic acid sequence (mRNA, RNA, DNA), an amino acid sequence corresponding to said nucleic acid sequence, or a combination of an amino acid sequence, nucleic acid sequence, and a non-natural molecule.

A "stalled" ribosome relates to a ribosome that is unable or that has otherwise been compromised so as to have a reduced activity for performing translation, relative to a conventional ribosomal translational activity and rate. By way of example, a stalled ribosome may comprise a ribosome that has a reduced activity for translation as a consequence of being bound to a nascent chain (protein, peptide, or other molecule), or as a consequence of having been aborted due to an encounter with a stalling element.

A "unique" restriction site relates to a restriction site on a nucleic acid sequence that is unique to a nucleic acid sequence, and particularly relates to a unique restriction endonuclease site present in a nucleic acid sequence of a plasmid.

A composition that is described herein as being "enriched" for a particular component or ingredient is defined as a composition having a greater concentration of the identified component or ingredient relative to the amount/concentration of that component in nature.

DESCRIPTION

While the present invention is not necessarily limited to such applications, various aspects of the invention may be appreciated through a discussion of various examples using this context.

Example 1

Material and Methods

The present example sets forth particular starting materials, reagents, and other materials, as well as the methods used in the description of the present invention.

Plasmids

The SecM gene was obtained from plasmid pNH21[14]. Preparation of plasmids encoding SecM stall fusion constructs is described in detail below.

Isolation of Ribosomes

E. coli strain BL21(DE3)pLysS, transformed with one of the SecM stall construct plasmids, was grown overnight at 37° C. in 25 ml of LB broth supplemented with 100 µg/ml ampicillin (Amp). A 100 mL volume of LB+Amp was inoculated with 2 ml of the overnight culture and grown for 3.5 hours at 30° C. Cultures were induced with 500 µM isopropyl-β-D-thiogalactopyranoside (Fisher®) and grown as before for an additional 30 minutes. Two 8 ml R buffer (50 mM Tris, pH 7.5, 10 mM $MgCl_2$, 150 mM KCl) ice cubes were added to each culture flask and the flasks were placed on ice to quickly cool the cultures to <4° C. Cell cultures from each flask (typically an equal volume of empty vector and tailspike-stall fusion cultures) were pelleted by centrifugation at 5000×g for 10 minutes. Pellets from each culture were resuspended in 200 µl of cold R buffer and transferred to a microcentrifuge tube. The resuspended cells were frozen at −80° C. for 30 minutes. Cells were lysed by thawing briefly in a room temperature water bath, adding 75 µl of 10 mg/ml lysozyme (Promega®), and incubating on ice for 15 minutes. A second freeze-thaw cycle resulted in efficient lysis.

To reduce the viscosity of the lysates, 50 µl of RNase-free DNase (Ambion®) and 50 µl of 1 M $MgSO_4$ was added and the lysates incubated for 15 minutes on ice. The lysates were spun at maximum speed for 5-8 minutes in a microcentrifuge at room temperature, until debris was well pelleted. Ribosomes were isolated from the cleared lysate in a procedure modified from Frydman et al.[6]: a 300 µl volume of cleared lysate was layered on top of a 2.5 ml 35% sucrose cushion prepared in R buffer. Samples were centrifuged for 15 minutes at a maximum RCF of 438,000×g in a Beckman Optima® MAX-E benchtop ultracentrifuge, using a TLA 100.3 rotor. Ribosomes were rinsed with cold R buffer, then resuspended in R buffer by gently swirling for 15 minutes at 4° C. For fluorescence measurements, cell lysates were labeled with 19 µM FlAsH dye (synthesized according to ref. 24) on ice for 1 hour. The lysate supernatants were then loaded onto 10-30% linear sucrose gradients prepared in R buffer. The gradients were centrifuged at 4° C. in a Beckman Optima®-L 90K ultracentrifuge to reach an accumulated centrifugal effect value of $2.3 \times 10^{11}$ $rad^2 \cdot sec^{-1}$. The gradients were then fractionated at 4° C. using an ISCO density gradient fractionation system (Teledyne® ISCO).

In Vitro Transcription/Translation Reactions

A T7 coupled transcription-translation system for circular DNA (EcoPro®, Novagen®) was used to generate stalled ribosome complexes in vitro. Reactions were prepared according to the manufacturer's directions, using 5 fYg of plasmid DNA supplemented with 1 fYl of RNAsin® (Promega®) and 3 fYg of the anti-ssrA oligonucleotide 5'-TTAAGCTGCTAAAGCG-TAGTTTTCGTCGTTTGCG-3' (SEQ ID NO: 11).

Reactions were incubated for 1 hour at 30° C. and quenched with 250 µl of ice-cold R buffer. Ribosomes were isolated by centrifugation through a sucrose cushion as described above.

Western Blotting

Western blotting was performed according to a procedure modified from Speed, M. A., et al (1997)[44]. A detailed procedure is included in the description below.

Plasmids

The SecM gene was obtained from plasmid pNH21[1]. A 285 nt segment corresponding to the 17 aa stall sequence, plus additional downstream regions, was amplified by PCR using primers:

5'-GGCGAGCTCTTCAGCACGCCCGTCTGG-3' (SEQ ID NO: 12) and
5'-GGCCTCGAGCTGCGCAACTGTTGGGAAGC-3' (SEQ ID NO: 13)

These primers incorporated SacI and XhoI restriction sites in the 5' and 3' ends of the amplified sequence, respectively. This PCR product was digested with SacI and XhoI (all restriction endonucleases were from New England Biolabs®) and ligated into pET21b/TSPK, a pET21b-based (Novagen®) plasmid containing the tailspike gene cloned between the NdeI and SacI restriction sites, also digested with SacI and XhoI. This vector, pET21b/TFSDE (Tailspike Full-length+Stall+Downstream Extension), was used as a template for site-directed mutagenesis (Quik-Change® Kit, Stratagene®) to introduce a new XhoI site immediately 3' of the stall sequence, using the following primers:
5'-GGCATCCGTGCTGGCCCTCTCGAG-CAACGCCTCACCTAACAA-3' (SEQ ID NO: 14) and
5'-GTTGTTAGGTGAGGCGTTGCTC-GAGAGGGCCAGCACGGATGCC-3' (SEQ ID NO: 15).

This vector now contained two XhoI sites flanking the 3'-SecM sequence not associated with translation stalling. Digestion with XhoI and subsequent religation of the vector eliminated the extraneous sequence, resulting in the vector pET21b/TFS, encoding the entire tailspike sequence minus the stop codon, Glu-Leu from the SacI restriction site, the 17 amino acids of the SecM stall sequence, the XhoI restriction site encoding a Leu and Glu residue, followed by the C-terminal six-histidine tag (SEQ ID NO: 16) and stop codon from the original pET21b vector. Other tailspike truncations [TfÖ (residues 1-556) and TS (residues 1-229)], tetraCys mutant sequences, and GFP truncation C-GFP49 were produced by PCR amplification of the desired sequence with a 5' primer incorporating the NdeI site, and a 3' primer complementary to the desired truncation point and incorporating the SacI restriction site. The GFP template was plasmid pcDNA-DEST53 (Invitrogen®). The PCR product was then ligated into the pET21b/TFS vector digested with NdeI and SacI, to replace the full-length tailspike sequence (TF) with the appropriate alternative sequence.

Western Blotting

Ribosomes were diluted in Laemmli sample buffer, boiled for 10 minutes, and the constituent proteins separated by denaturing polyacrylamide gel electrophoresis[2] using a 4-15% acrylamide gradient gel (Bio-Rad). Gel contents were transferred to a PVDF membrane using a Criterion Electroblotter® (Bio-Rad®) under a constant voltage of 25 V for 16 hr at 4° C. Following transfer, membranes were blocked in TBST buffer (20 mM Tris, pH 7.5, 150 mM NaCl, 0.5% Tween 20) containing 5% powdered dry milk (PDM) for 50 minutes while rocking at room temperature. Membranes were incubated for 50 minutes with a primary antibody cocktail consisting of the anti-tailspike monoclonal antibodies 70 and 92[3] in 30 ml TBST+2% PDM. The blot was then washed twice with TBST for 5 minutes.

A secondary antibody solution containing a 1:20,000 dilution of goat-anti-mouse IgG-alkaline phosphatase conjugate (Southern Biotechnologies) in TBST supplemented with 2% PDM was incubated with the blot for 30 minutes while rocking. The blot was again washed twice with TBST for 5 minutes. Finally, color was developed by adding an alkaline phosphate substrate solution containing 66 µl nitro blue tetrazolium (Promega®) and 35 µl 5-bromo-4-chloro-3-indolyl-phosphate (Promega®) in 10 ml AP buffer (100 mM Tris, pH 9.5, 100 mM NaCl, 5 mM MgCl$_2$). The color development step proceeded for 10-20 minutes. Blots were scanned and band densities quantified using ImageJ® software for MacOS X® (NIH; http://rsb.info.nih.gov/ij/).

Example 2

In-Gel Detection of Fluorescently Labeled Nascent Chains

The Lumio Green Detection® Kit (Invitrogen®) was used to visualize the C-GFP49 nascent chain in a denaturing polyacrylamide gel. Sample preparation and visualization were performed according to the manufacturer's protocol. Briefly, resuspended ribosomes were mixed with Lumio gel sample buffer and labeled by mixing with 20 µM FlAsH. This was followed by incubation at 70° C. for 10 min. The samples were cooled to room temperature, mixed with the in-gel detection enhancer, incubated 5 min at room temperature, and the constituent proteins separated by denaturing polyacrylamide gel electrophoresis[31] using a 14% acrylamide gel (Bio-Rad®). Bands were visualized using a UV transilluminator equipped with a digital camera (Kodak®). The gel image was digitized using an ethidium bromide filter with a 10 second exposure.

Fluorescence Measurements

Sucrose gradient fractions were diluted 1:5 in R buffer and fluorescence excitation and emission spectra were measured using a PTI QM-6 fluorescence spectrometer. Fluorescence emission was scanned from 520-600 nm with a constant excitation wavelength of 505 nm. Excitation and emission slit widths were 5 nm. Samples were measured in quartz cuvettes, and a circulating water bath was used to maintain the temperature at 25° C. The fluorescence intensity at the wavelength of maximum emission (528 nm) was recorded for each fraction.

Antibody Binding Measurements

A dilution series of ribosomes bearing TFS, TβS or TSS nascent chains was prepared and the binding of mAb 236 was measured using the competition ELISA test[25,26]. Concentrations of nascent chains were determined as described for calculations of stalling efficiency (see Example 6, paragraph 0094). mAb 236 binding to native tailspike trimer was also determined, as described previously[17]. Data were fit by non-linear regression to the equation:

$$f = \frac{x}{x + K_d}$$

where f represents the fraction of bound antibody and x is the nascent chain concentration.

Example 3

SecM-Directed Production of Stalled Ribosome Complexes

To exploit the SecM 17 aa stall sequence as a general tool to create stalled ribosome complexes bearing nascent chains of any sequence in vivo, three modified expression plasmids were created to insert the SecM stall sequence at three different places in the sequence of phage P22 tailspike (FIG. 1B; also see Example 1).

Tailspike is a homotrimeric parallel β-helix protein previously shown to form some native-like structure while nascent chains are still attached to the ribosome[8,15]. The longest tailspike nascent chain construct (TFS) was designed so that the almost all of the monomer would be exposed from the ribosome, with only the C-terminal ~20 aa occluded in the ribosomal exit tunnel. The mid-length (TβS) and shortest (TSS) nascent chain constructs were designed to expose the entire β-helix domain or the first three rungs of the β-helix domain, respectively, outside of the ribosome tunnel.

Figure 2A:
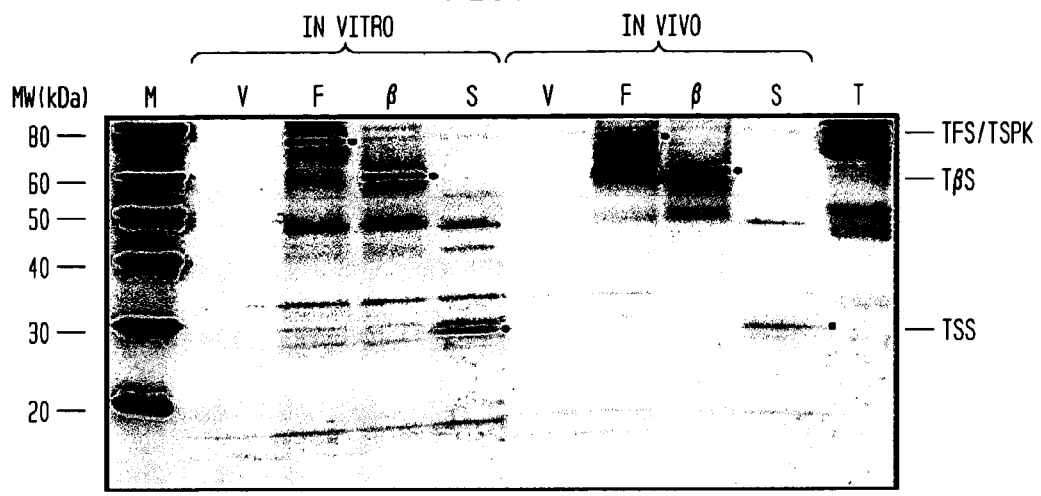
FIG. 2A-2B, in accordance with one embodiment of the invention, presents SDS-PAGE separation of stalled ribosome-nascent chain complexes, detected by western blotting using anti-tailspike monoclonal antibodies (A), or the Lumio in-gel detection system (B). (2A) TFS, TβS and TSS stalled nascent chains were detected on ribosomes derived from E. coli cultures (in vivo) or from coupled transcription-translation reactions (in vitro). M, molecular weight markers. T, full-length purified tailspike monomer. Other lanes depict ribosomes derived from cells expressing (or in vitro translation reactions programmed with): V, empty vector; F, TFS; β, TβS; or S, TSS. This figure is a composite of two western blots produced under identical conditions, one for in vitro samples, and one for in vivo samples. Bands for in vitro samples appear darker than in vivo samples only because in vitro ribosomes were resuspended in a smaller volume of buffer. (2B) C-GFP49 nascent chains were detected on ribosomes derived from E. coli cultures as described for tailspike nascent chains. V, empty vector; G, C-GFP49. Dots indicate the expected sizes of tailspike and GFP nascent chains.

E. coli cells were then transformed with one of three plasmids encoding tailspike/SecM stall fusion constructs. Protein expression was induced with IPTG, and cells were lysed using a combination of lysozyme treatment and freeze-thaw cycles. Ribosomes were separated from other components of the cell lysate supernatant by centrifugation through a sucrose cushion. Tailspike nascent chains were resolved by SDS-PAGE and western blotting using two anti-tailspike monoclonal antibodies (mAbs) with epitopes in the tailspike N-terminal domain (residues 1-109, FIG. 1C)[16,17]. Discrete bands, corresponding to each of the tailspike nascent chain lengths, were observed in the ribosome preparations (FIG. 2A). Faint bands corresponding to shorter tailspike fragments were also detected; in many cases these chain lengths correlate with endogenous translation pause sites. Other bands, particularly those at ~33 kDa and <20 kDa, were also detected in empty vector lysates, and are most likely due to non-specific antibody binding. Other faint bands might arise from nascent chain degradation fragments, and/or nascent chains still attached to tRNAs.

To ensure that the truncated tailspike bands observed did not arise from chains released from the ribosome, a lysate from *E. coli* cells transformed with the empty vector was spiked with purified native tailspike and the ribosomes isolated as before. No tailspike was detectable by western blotting in the resuspended ribosomes, indicating that released TFS, TβS or TSS chains, which are all smaller than native tailspike, were unlikely to sediment.

SecM-directed production of stalled ribosome-nascent chain complexes was also measured in commercial *E. coli* coupled transcription-translation lysates, each programmed with a plasmid encoding one of the three tailspike/SecM stall fusions. In all reactions, an oligonucleotide complimentary to the ssrA RNA sequence was included to suppress the release of stalled nascent chains[18]. Ribosomes were isolated and analyzed as described above. As with in vivo translation, each of the tailspike nascent chain lengths was detectable by western blotting, with minimal background from other tailspike translation products (FIG. 2A).

Example 4

SecM-Directed Stalling of Short Nascent Chains

SecM-directed translation stalling was also examined using a sequence, CGFP49, which consists of the tetraCys FlAsH binding motif (CCPGCC)(SEQ ID NO: 10) followed by the Nterminal portion of green fluorescent protein (GFP)[19] (residues 1-64), and the SecM stall sequence (FIG. 1B). The biarsenical fluorescein derivative FlAsH binds specifically to this optimized tetraCys motif20, and upon binding FlAsH fluorescence emission intensity increases dramatically[21].

Figure 2B:
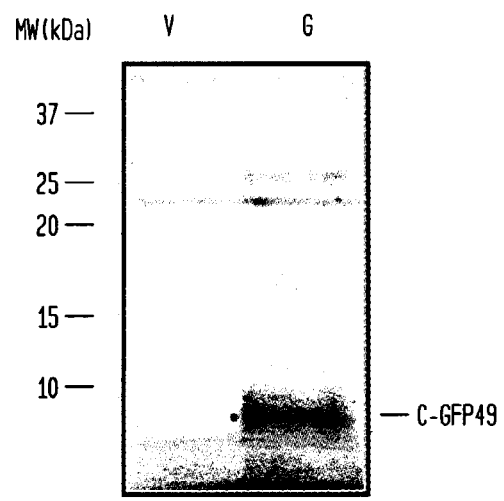

Stalled C-GFP49 was detected by fluorescence emission after denaturing gel electrophoresis of ribosomes prepared from *E. coli* cultures (FIG. 2B), as were bands corresponding to two larger species (~23 and 27 kDa). The 23 kDa band was present in both the empty vector control and C-GPF49 lanes, and is most likely SlyD, an endogenous *E. coli* metal binding protein with high affinity for the FlAsH dye[22]. The 27 kDa band may represent C-GFP49 still attached to tRNA, or multimeric C-GFP49 nascent chains. Multimerization of C-GFP49 chains at the tetra-Cys motif via disulfide bond formation is known to occur during sample processing[20]. Nevertheless, the major band is the expected 9.4 kDa monomeric C-GFP49.

Example 5

Separation of Stalled Ribosomes from Released Chains

Figure 3A:
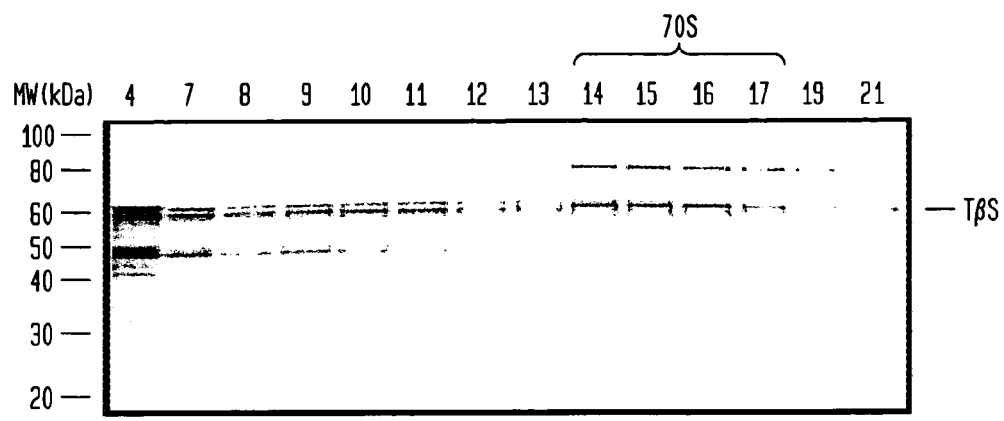
FIG. 3A-3B, in accordance with one embodiment of the invention, presents TβS nascent chains associated with ribosomes. (3A) Lysates of E. coli cultures expressing TβS were separated by sucrose density gradient centrifugation, and the gradient was fractionated. TβS was detected by western blotting as in FIG. 2. TβS is present in top gradient fractions (released chains) and 70S fractions. (3B) $A_{254}$ profile of gradient fractions, showing accumulation of 70S ribosomes in fractions 14-17.
Figure 3B:
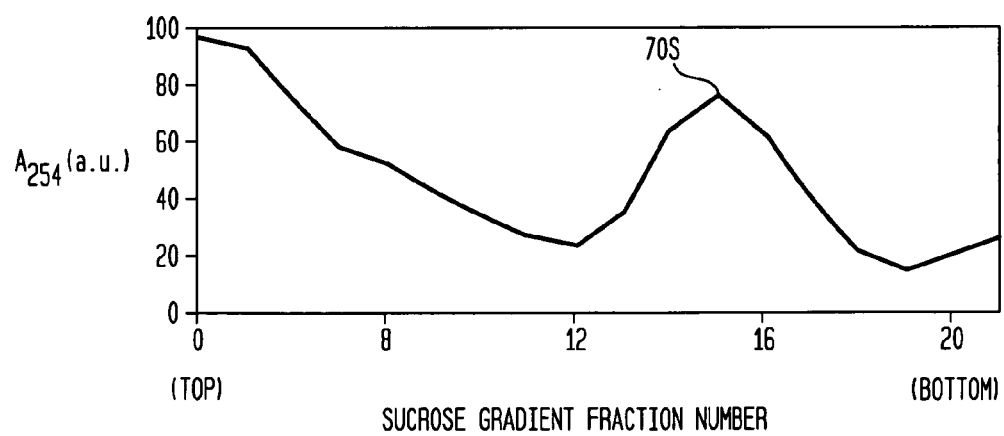

To further verify that tailspike nascent chains were ribosome-associated, a lysate from *E. coli* expressing TβS was separated on a 10-30% sucrose gradient (FIG. 3). An intense band at 60 kDa, corresponding to released TβS, was detected in top gradient fractions. Some level of released chains was expected, given the relatively long (30 minute) induction time. The TβS band decreased in intensity until 70S fractions, where the intensity increased sharply. A band at 80 kDa also appeared in 70S fractions, and may represent TβS nascent chains still attached to tRNA. The 47 kDa band present in fractions 4-12 is most likely the result of proteolytic degradation of released TβS.

Example 6

Nascent Chain Stalling Efficiency

To demonstrate the efficiency of SecM-directed stalling in vivo and in vitro, the percentage of ribosomes bearing a stalled nascent chain using the constructs described herein was calculated. The amount of stalled tailspike nascent chain detected by western blotting was determined by comparison with a purified tailspike dilution series, and the total concentration of ribosomes was determined using the relationship 1 $A_{260}$ unit=23 pmol 70S ribosomes[23].

The percentage of ribosomes bearing a stalled tailspike nascent chain is given in Table 1.

TABLE 1

SecM-directed translation stalling efficiency in vivo and in vitro.

| Nascent chain | Length to stall point (aa) | mAb 236 $K_d$ (nM) | % Stalled in vitro$^a$ | % Stalled in vivo$^a$ |
|---|---|---|---|---|
| TFS | 685 | 3 ± 1 | 21 ± 1 | 26 ± 4 |
| TβS | 575 | 6 ± 4 | 23 ± 1 | 52 ± 16 |
| TSS | 248 | 0 | 34 ± 3 | 13 ± 4 |

$^a$Values reported are the average of three determinations. Error is given as the standard deviation from the mean.

In general, stalling was even more efficient in vivo than in vitro. Stalled ribosomes represented between 13 and 52% of the total ribosome pool, depending on the stall construct used.

Example 7

Nascent Chain Detection by FlAsH fluorescence

Figure 4A:
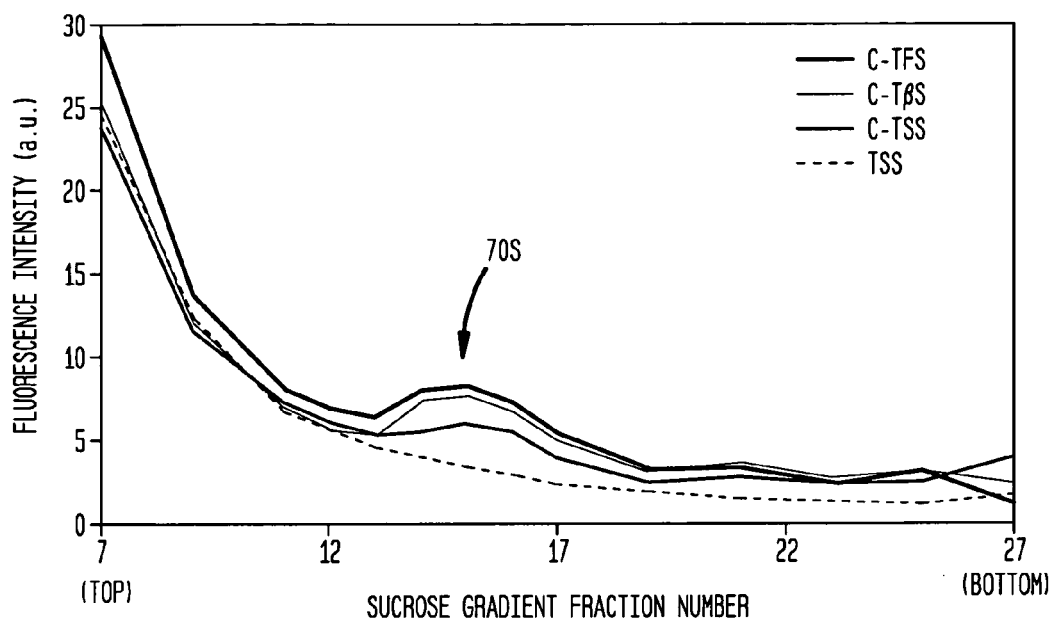
FIG. 4A-4B, in accordance with one embodiment of the invention, illustrates stalled ribosome-nascent chain complexes detected by FlAsH binding. Lysates from cells expressing C-TFS ("C" denotes incorporation of the CCPGCC (SEQ ID NO: 10) FlAsH binding motif as shown in FIG. 1C), C-TfOS, C-TSS, TSS, C-GFP49, or empty vector were separated by sucrose density gradient fractionation, and the fluorescence of the gradient fractions was measured. Fractions containing ribosomes, as judged by their absorbance at 254 nm ($A_{254}$) and sedimentation position (70 S), showed a peak in FlAsH fluorescence emission intensity. Cells expressing TSS chains, lacking the FlAsH binding motif, or empty vector, emitted considerably less fluorescence in ribosome-containing fractions. (4A) Tailspike nascent chains. (4B) GFP nascent chain.
Figure 4B:
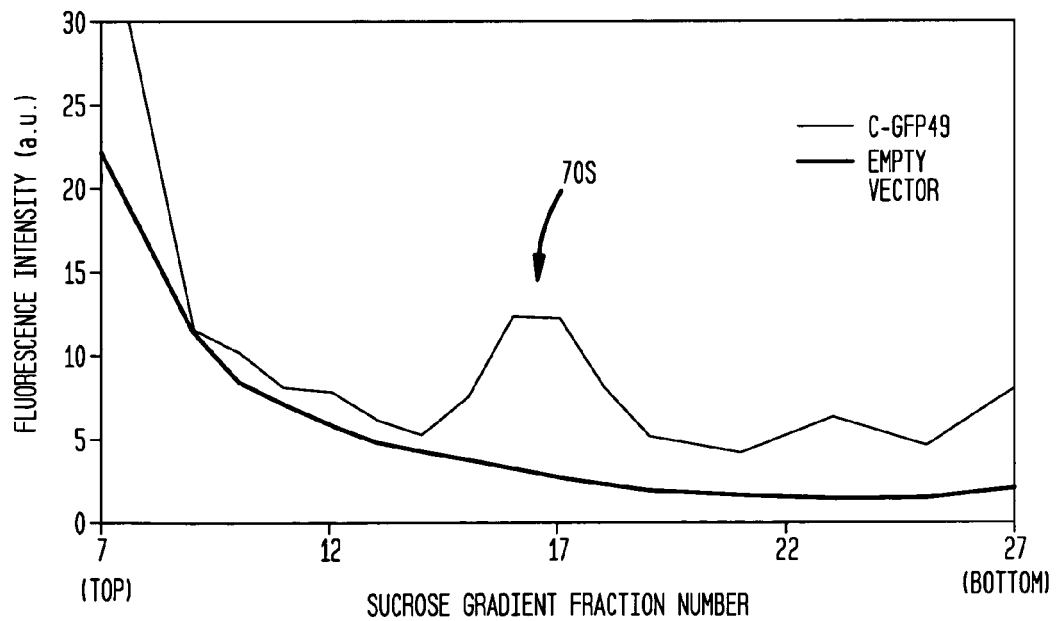

As an alternative method to detect nascent chains on stalled ribosomes, the tetraCys FlAsH binding motif was introduced into the tailspike sequence, replacing residues 102-107 at the proteolytically labile junction between the N-terminal domain and the central β-helix domain[24], producing constructs C-TFS, C-TβS, and C-TSS (FIG. 1C). Each lysate was labeled with FlAsH, and stalled ribosome-nascent chain complexes were prepared by centrifuging cell lysate supernatants through sucrose density gradients. A fluorescence emission maximum was observed at ~528 nm for all fractions, as previously described for FlAsH[21]. Fluorescence emission intensity was maximal in top gradient fractions (corresponding to excess free FlAsH) and decreased along the gradient, with the exception of an emission peak in 70S ribosome-containing fractions (FIG. 4A). FlAsH-labeled C-GFP49 lysates were also separated on sucrose gradients, and the fluorescence emission of gradient fractions was measured. As for stalled tailspike chains, there was a distinct peak of FlAsH fluorescence in ribosome-containing fractions (FIG. 4B).

Example 8

Measuring Co-Translational Tailspike β-Helix Folding

The present example demonstrates the utility of the invention for providing a large number of stalled ribosome:nascent chain complexes having a uniform nascent chain component in a cell (in vivo).

One advantage of producing stalled ribosome-nascent chain complexes in vivo is the ability to easily and inexpensively produce large amounts of stalled nascent chains for biophysical assays. For example, a panel of anti-tailspike monoclonal antibodies have been characterized that are sensitive to changes in tailspike conformation during in vitro refolding[15,17]. One such antibody, mAb 236, recognizes native trimeric tailspike with sub-nanomolar affinity, yet shows no affinity for early in vitro refolding intermediates[17]. The mAb 236 binding epitope is located in the center of the tailspike β-helix domain (FIG. 1C)[17], completely contained within the sequence of the TFS and TβS constructs.

Figure 5:
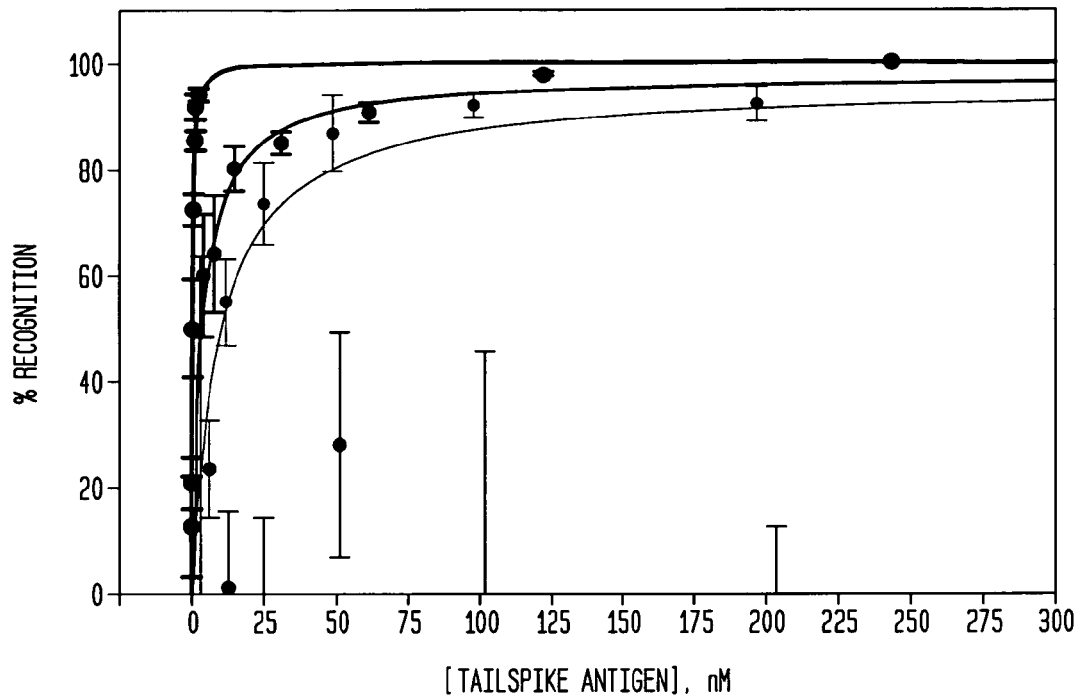
FIG. 5, in accordance with one embodiment of the invention, presents measurements of mAb 236 binding to stalled tailspike nascent chains and native tailspike trimer: TFS (bottom curve), TβS (bottom curve), TSS (unconnected points/error bars bars at about 15 nM, 25 nM, 50 nM, about 101 nM, about 205 nM), native tailspike (top curve). The connection of native tailspike is expressed as the concentration of trimer, while the concentration of nascent chains is expressed as the concentration of monomer. Data shown are from one representative competition ELISA study; measurements for each concentration were performed in triplicate. Error bars represent the standard deviation between the triplicate measurements. Due to the larger error inherent to measuring very low or zero amounts of binding, some TSS data points lie beneath the X-intercept. Lines represent the best fit to the data using the equation described herein.
Figure 6:
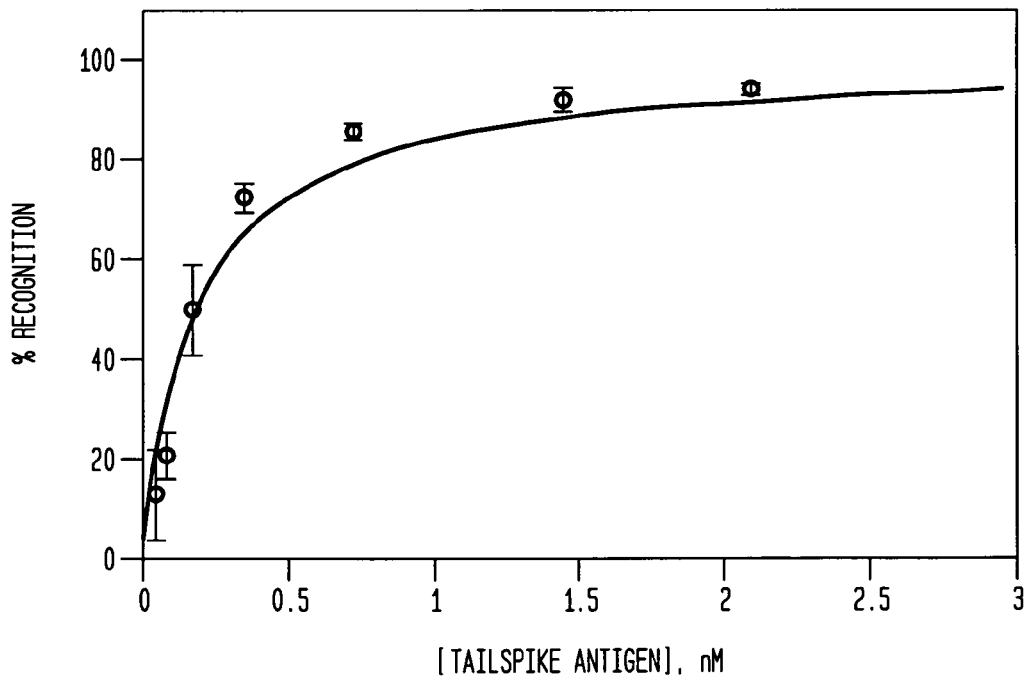
FIG. 6, in accordance with one embodiment of the invention, demonstrates mAb 236 binding to native tailspike trimer, using an expanded x-axis scale.

To determine a dissociation constant ($K_d$) for the binding of mAb 236 to each of the tailspike nascent chain lengths, serial dilutions of ribosomes bearing each construct were prepared and mAb 236 binding was measured using a competition ELISA test[25,26]. The mAb 236 showed no affinity for the shortest construct (TSS), which lacks the mAb 236 epitope (FIG. 5). However, mAb 236 bound tightly to TβS and TFS tailspike nascent chains ($K_d$=6±4 and 3±1 nM, respectively), in contrast to the complete lack of mAb 236 binding to early tailspike in vitro refolding intermediates[17].

Example 9

Ribosome Display

The present example demonstrates the utility of the invention for use in creating a ribosomal display. These ribosomal displays have many utilities, including utility in the creation of a library of selectable mRNAs encoding proteins or peptides of interest, such as an mRNA library encoding mutant proteins of interest. From these libraries, mRNAs encoding a desired protein or peptide may be selected and sequenced to identify the corresponding DNA sequence using PCR-based amplification. These and other applications will be appreciated from a reading of the following example.

Ribosome display of peptides and proteins for genetic selection was pioneered by Andreas Plückthun (Univ. Zurich, Switzerland). In Plückthun's approach, a DNA library encoding mutated sequences of a protein of interest, followed by a C-terminal spacer, is transcribed in a cell-free system. This transcribed mRNA lacks a stop codon, because the stop codon has been deleted from the DNA sequence (i.e., there is no stop codon prior to the transcription termination point). The mRNA library is then translated, again using a cell-free system. Translation proceeds to the end of the mRNA, then stalls because there is no (i) RNA to translate or (ii) stop codon to dissociate the ribosome.

The resulting ternary mRNA:ribosome:nascent protein complex is stable for up to 10 days, and due to the C-terminal spacer, the translated protein is completely emerged from the ribosome exit tunnel and able to fold to an active conformation. The protein can then be used for screening, for example by passing the library of mutant ternary complexes over a column of an immobilized drug or other binding partner. The ternary complexes that survive the screen are next destabilized by EDTA, and the gene sequences of the mutants may be amplified by reverse transcription and PCR (RT-PCR). Additional rounds of PCR, to produce a 'second generation' ribosome display library, can then begin. However, these additional rounds of PCR are prone to error.

Plückthun has described approaches to improve the stability of the ternary complexes. Some examples of these include:
- stem-loop structures at the 5'- and 3"-ends of the mRNA (to inhibit ribonucleases), and
- quenching the translation reactions using low temperature and/or high [Mg2+] (to increase the stability of the ribosomes), and
- addition of an ssrA/tmRNA antisense oligonucleotide (to inhibit an *E. coli* mechanism to release stalled ribosomes).

The approach works using the common translation systems from prokaryotic (for example, *E. coli*) and eukaryotic (for example, yeast, rabbit reticulocytes, wheat germ) sources.

Plückthun's approach requires mRNA transcription be performed as a separate reaction. This separate reaction step requires handling and stabilizing fragile mRNA pools. In contrast, the cell-free systems described here using stall element (such as, for example, SecM) directed ribosome stalling can be accomplished using coupled transcription/translation lysates, eliminating the need for a separate transcription reaction. Alternatively, transcription and translation can be accomplished in vivo (in a cell), eliminating altogether extracellular exposure of the mRNA.

In addition, Plückthun employs a system that uses an mRNA that lacks a stop codon, as well as other 3' downstream regions. Because of this, ribosome initiation is inefficient. Phückthun includes a downstream transcriptional termination site (as opposed to other mechanisms that merely truncated an intact mRNA) in an effort to remedy this deficiency. However, efficiency is still not as improved as the approach provided here, that does not employ a truncated mRNA and that does use an mRNA having a stop codon and naturally occurring 3'-mRNA sequence.

The mRNAs of the present methods and compositions have a stop codon (downstream of the stall element sequence), and all other features of 'normal' mRNA. These features, among others, contribute to an even further improvement in translational efficiency.

In an alternative aspect, the method of the present invention may be practiced using a coupled transcription/translation in vitro step, or as a coupled transcription/translation in vivo (in a cell) step. This presents an advantage over the technique described in Plückthun where transcription was carried out as a separate reaction.

By way of example, a ribosome display in vivo may be provided by replacing the below described steps 1 and 2 with a coupled transcription/translation in vivo step to create transformed cells (using a construct including the stall element (such as the stall elements described herein modeled after SecM), inducing expression of the transformed cells, and lysing the transformed cells to produce a pool of stalled ribosome:nascent chain complexes.

Creation of a Ribosome Library Utilizing a Stall Segment Ribosome Model

Step 1. A library of DNA is transcribed by an in vitro transcription system to provide a pool of candidate mRNAs. This library may contain random or directed (specific) mutants or may be made from the cellular mRNA population (cDNA library), with all the sequences containing a 3' SecM sequence.

Result: Transcription of the DNA library yields a pool of candidate mRNAs for the ribosome library that include a stall element sequence.

Step 2. The pool of candidate mRNAs are introduced into an in vitro translation system to provide a pool of stalled ribosome:nascent chain molecule complexes.

Result: The pool of candidate mRNAs are translated and yield a pool of ribosomes with a nascent chain attached. This chain is stalled at the SecM sequence, with the target molecule (e.g., protein) exposed outside the ribosomal tunnel.

At this step, a ribosome display of selected mRNA species is provided.

Step 3. The pool of stalled ribosome:nascent chain complexes are exposed to a selective agent (substrate, binding protein or antibody) having affinity for the nascent chain of interest.

Result: The stalled ribosomes with bound nascent chain having the phenotypic property desired (i.e., binding to a substrate) can be isolated from the general population of ribosomes to provide a selected pool of stalled ribosome: nascent chain complexes having a desired nascent chain of interest. This may be achieved using a resin or affinity column that contains a substrate, binding protein or antibody specific for the nascent chain of interest. Ribosomes with no nascent chains or undesired nascent chains are eluted away from the ribosomes with target nascent chains.

The following additional steps may be performed in order to obtain selected DNA sequences corresponding to the subject selected mRNAs of the stalled ribosome complexes.

Step 4. Selected pool of stalled ribosome:nascent chain of interest complexes are denatured with mild detergent or heat, and/or EDTA.

Result: The ribosomes are denatured and the selected mRNAs (having a stall tag (SecM) sequence) are freed from the complex.

Step 5. Reverse-transcription polymerase chain reaction (RT-PCR) of the freed mRNAs to produce DNA.

Result: Reverse-transcription polymerase chain reaction (RT-PCR) produces a DNA product using a primer that binds specifically to the 3' end of the selected mRNA (stall tag).

A limitation to Plückthun-style ribosome display is the repetitive linker sequence immediately 3' to the sequence of interest; it is very difficult to design a specific primer binding site in this region. In contrast, the stall tag (for example, a stall tag having a sequence modeled after SecM) sequence at the end of the selected mRNA provides a specific primer binding site.

Step 6. Sequencing of DNA and sequence alignments

Result: The DNA sequences prepared from the targeted mRNAs are obtained and compared to define DNA sequences and to identify important residues contained therein.

In contrast to standard ribosome display, stall element (SecM)-mediated ribosome display enables the creation of screenable mRNA libraries containing a 3' conserved element (for example, a stall element having a sequence modeled after the stall [SecM] sequence) that is particularly valuable for RT-PCR and sequencing.

Example 10

In Vivo Screening with Stall Element and Constructs Thereof

While the absence of transformation into cells is sometimes regarded as an advantage of Plückthun-style ribosome display, this may be due to the inability to produce stalled chains in vivo because these techniques employ mRNAs lacking a stop codon. Since the use of a stall element and mRNA species having a stop codon can be efficiently used with the presented methods, in vivo transformation of cells is an available option for ribosomal display.

In vivo, the cellular machinery (including, but not limited to, molecular chaperones that assist folding) that increase protein folding or modify nascent chains is present to participate and to provide previously unavailable and unknown results. Furthermore, for nascent chains that result in poor yields of folded product while tethered, the significantly higher number of ribosomes in vivo vs. in vitro may be expected to increase the population of properly folded chains to identify novel sequences.

Example 11

Eukaryotic Stall Sequences

The present example demonstrates the utility of the present invention for providing a eukaryotic stall element, and for its use in the creation of eukaryotic stalled ribosome:nascent chain complexes.

The SecM stall sequence is found only in eubacteria (for example, *E. coli* and *Salmonella*). No BLAST hits were found to other proteins. The SecM stall sequence is near the C-terminus of SecM, and upon translation of the stall sequence, about 150 aa of SecM are outside the ribosome tunnel. While eukaryotic systems do not use an endogenous SecM-related stalling mechanism, there are several other mechanisms known to stall translation in eukaryotes and prokaryotes.

One eukaryotic downstream stall element is CGS1. This stall element has a native sequence of RRNCSNIGVAQ (SEQ ID NO: 17). In the present example, a eukaryotic stall element modeled after this sequence is presented. It is envisioned that one such construct may comprise a sequence of Formula II:

X1-RR-X3-Q-X2, wherein X1, X2 or both X1 and X2 comprise 1 or more histidine residues. X1 may comprise an amino acid residue such as A (alanine). X2 may comprise an amino acid residue such as I (isoleucine). X3 may comprise one or more amino acid residues other than the sequence NCSNIGVA (SEQ ID NO: 8)

In at least one case, using arg-2, effective ribosome stalling was observed using the arg-2-stall sequence moved to a C-terminal downstream position.

Some additional potential eukaryotic ribosome stall elements may be fashioned using the identified elements and sequences presented below, such as, for example, gp48, CPA 1 and arg-2. Mutations of the residues in bold reduce/eliminate ribosome stalling. In creating a potential eukaryotic stall element, it is important to consider that these bolded residues may not be the only residues involved in stalling.

Using arg-2, others have shown that stalling is effective using a variety of eukaryotic, but not prokaryotic translation systems. This suggests the lining of the ribosome exit tunnels on prokaryotic and eukaryotic ribosomes might be different enough to require different sequences for effective stalling. The arg-2 also requires arginine depletion for effective stalling. These and other modifications may be made in adapting the herein described ribosome stalling approaches to use in a eukaryotic system (cell and/or extract).

Eukaryotic Peptide Stall Segments:
1. Protein: CMV UL4 (gp48)
Peptide sequence: (codons 1-22 from uORF2):
MQPLVLSAKKLSSLLTCKYIPP (SEQ ID NO: 18)
The gene origin of this sequence is a mammalian virus The ribosome translates through uORF2 until the uORF2 peptide attached to the cognate tRNAPro for the terminal proline codon (CCU) is positioned in the ribosomal P site, while the stop codon (UAA) is in the A site. At this point eRF1 enters the ribosomal A site, recognizes the stop codon, and binds to the ribosome. During the termination reaction, the glycines of the eRF1 GGQ motif and the two terminal prolines of uORF2 interact, possibly through the peptidyltransferase, to form an intermediate that stabilizes the peptidyl-tRNA bond. This stabilization contributes to prolonged ribosomal stalling, which in turn blocks ribosomes from scanning to the downstream UL4 cistron (See Janzen et al. (2002)[37]).

2. Protein: CPA1
Peptide sequence: (codons 1-25 from uORF):
MFSLSNSQYTCQDYISDHIWKTSSH (SEQ ID NO: 19)
The gene origin of this sequence is fungi The nascent uORF-encoded peptide acts on its translating ribosome and prevents release at the termination codon for the uORF.
This stalled ribosome sets up a blockade to ribosome scanning, preventing initiation of translation of downstream coding sequence (See Lovett et al., (1996)[38]; Morris et al. (2000)[39]).

3. Gene: arg-2 (encode CPA1 analog)
Peptide sequence: (codons 1-24 from uORF):
MNGRPSVFTSQDYLSDHLWRALNA (SEQ ID NO: 20)
The gene origin of this sequence is fungi. arg-2 is also called arginine attenuator peptide (AAP). It uses Arg as a co-activator. Stalling at both the N-terminal and internal positions has been reported (hence, some similarities with SecM mechanism). It also works in plants and animal systems (See Fang et al., (2004)[45], Lovett et al. (1996)[38] and Morris et al. (2000)[39].

4. Gene: CGS 1 (encodes cystathionine-synthase)
Peptide sequence:
76-(A)RRNCSNIGVAQ(I)-78 (SEQ ID NO: 21),
the first and last residues (in brackets) may vary. Also called MTO1 region.
The gene origin of this sequence is a plant. Translation elongation arrest is at the Ser-94 codon located immediately downstream of the MTO1 region. This translation arrest precedes the formation of a degradation intermediate of CGS1 mRNA, which has its 5' end points near the 5' edge of the stalled ribosome. The position of ribosome stalling also suggests that the MTO1 region in nascent peptide resides in the ribosomal exit tunnel when translation elongation is temporarily arrested.
The addition of S-adenosyl-L-methionime is required for MTO1 stalling. In addition to the MTO1 region amino acid sequence, downstream Trp-93 is also important for the AdoMet-induced translation arrest. This demonstrates nascent peptide-mediated translation elongation arrest coupled with mRNA degradation in eukaryotes. Furthermore, this data suggest that the ribosome stalls at the step of translocation rather than at the step of peptidyl transfer.
The MTO1 region is conserved among CGS sequences of higher plants but cannot be found elsewhere in the public databases (See Ominato et al. (2002)[40]; and Onouchi et al. (2005)[41]).

Example 12

Medical Applications

There is a growing realization that many human diseases are caused by protein folding defects in vivo. In addition, there is a growing interest in producing a wider range of proteins for therapeutic purposes. The present example defines the utility of the present invention for providing a useful mechanism for use in identifying and/or treating human diseases and for screening/identifying potentially potent new pharmaceutical products.

Antibiotics/Antibacterial Agents

An essential component of effective antibiotics is the ability to exploit and destroy an essential bacterial process or mechanism that is not used by eukaryotic cells. For example, many common antibiotics (penicillin, etc.) are small organic molecules that bind to the proteins that are responsible for synthesizing the rigid cell wall that is unique and essential to bacterial cells. From this perspective, if the SecM stall sequence is effective at stalling ribosomes from bacterial cells, but has no effect on eukaryotic cells, then SecM-mediated stalling could be adapted to stall bacterial ribosomes to such a large degree that there are not enough free, unstalled ribosomes left to synthesize the proteins essential to bacterial cell viability.

Nakatogawa et al. (2002)[33] report very short nascent chains bearing the SecM stall sequence (basically, those that start immediately with the stall sequence) have a negative effect on bacterial cell viability. Given the disclosure provided here on the use of SecM modeled stall sequences for stalling prokaryotic ribosomes, the SecM stall sequence may provide an effective antibiotic and/or antibacterial agent.

Gene Therapy in Eukaryotic Cells

SecM stall sequence or an alternative sequence (for example, a stall element having a sequence based on one of the eukaryotic sequences presented in Example 11), once demonstrated to be effective at stalling translation in eukaryotic cells can provide the potential for using SecM directed translation stalling in gene therapy applications. For example, there are many diseases that arise due to the aberrant overproduction of a particular protein or proteins.

The stall element constructs may be used in gene therapy to introduce a stall sequence at the C-terminus of such a protein, reducing its accumulation. However, this treatment would be most effective only if there were not several genes or other factors that led to the over-accumulation of the causative protein. If there were only one gene responsible, and gene therapy was an effective treatment, it would be easier to use gene therapy to remedy a gene defect or activity responsible for the protein overproduction.

Example 13

Degradation Tag containing Stall Element Constructs

The present example is presented to describe those embodiments of the constructs that include a C-terminal or an N-terminal modification of the stall element. In some examples, this C-terminal modification comprises a degradation tag.

One well-characterized degradation tag (sequence) in bacteria is 'ANDENYALAA' (SEQ ID NO: 7). This sequence is added, by a mechanism called ssrA, to the C-terminus of nascent proteins targeted for degradation. Expressing a protein with this sequence already encoded at the C-terminus (rather than having it added by ssrA) has been shown to trigger rapid degradation of the protein (Hayes et al. (2002)[43].

In eukaryotes, the primary focus for degradation is governed by a principle known as the "N-end rule", meaning that the N-terminal residues play a key role in determining how fast the protein will be ubiquitinated, a covalent modification that targets a protein for degradation. Different N-terminal residues result in faster degradation in different species (yeast vs. human, etc.). In general, the most effective N-end rule sequence is 'RK'. The N-rule can also be used to control protein half-life in bacteria.

Degradation can be further enhanced by placing an unstructured, floppy sequence between the N-end rule amino acids and the start of the true, structured protein. The floppy sequence will make it easier for the proteasome (the protease that degrades cellular proteins) to latch onto the protein and initiate degradation.

In eukaryotic systems, many proteins are sent to other organelles (ER, golgi, etc.), and then pumped back into the cytoplasm for degradation by the proteosome. There are post-translationally added sequences ('KDEL' (SEQ ID NO: 22), for example) which, when added to the C-terminus of a protein, will keep a Golgi-destined protein in the ER for longer than usual, usually because the protein is taking longer than usual to fold correctly.

It is believed that KDEL (SEQ ID NO: 22) tag will also decrease the half-life of ER proteins; again, the tag serves as a quality control mechanism.

BIBLIOGRAPHY

The following references are hereby incorporated by reference herein.
1. Nissen, P., et al. (2000), *Science*, 289; 920-930.
2. Berisio, R. et al. (2003), *Nat Struct Biol*, 10; 366-370.
3. Malkin, L. I. & Rich, A. (1967), *J Mol Biol*, 26; 329-346.
4. Woolhead, C. A., et al. (2004), *Cell*, 116; 725-736.
5. Komar, A. A., et al. (1997), *J Biol Chem*, 272; 10646-10651.
6. Frydman, J., et al. (1999), *Nat Struct Biol*, 6; 697-705.
7. Nicola, A. V., Chen, W. & Helenius, A. (1999), *Nat Cell Biol*, 1; 341-345.
8. Clark, P. L. & King, J. (2001), *J Biol Chem*, 276; 25411-25420.
9. Fedorov, A. N. & Baldwin, T. O. (1999), *J Mol Biol*, 294; 579-586.
10. Clark, P. L. (2004), *Trends Biochem Sci*, 29; 527-534.
11. Ghaemmaghami, S. & Oas, T. G. (2001), *Nat Struct Biol*, 8; 879-882.
12. Dedmon, M. M., et al. (2002), *Proc Natl Acad Sci USA*, 99; 12681-12684.
13. Ignatova, Z. & Gierasch, L. M. (2004), *Proc Natl Acad Sci USA*, 101; 523-528.
14. Nakatogawa, H. & Ito, K. (2002), *Cell*, 108; 629-636.
15. Friguet, B., et al. (1994), *J Biol Chem*, 269; 15945-15949.
16. Friguet, B., et al. (1990), *J Biol Chem*, 265; 10347-10351.
17. Jain, M., Evans, M. S., King, J. & Clark, P. L. (2005), *J Biol Chem*, 280; 23032-23040.
18. Hanes, J. & Pluckthun, A. (1997), *Proc Natl Acad Sci USA*, 94; 4937-4942.
19. Crameri, A., Whitehorn, E. A., Tate, E. & Stemmer, W. P. (1996), *Nat Biotechnol*, 14; 315-319.
20. Adams, S. R. et al. (2002), *J Am Chem Soc*, 124; 6063-6076.
21. Griffin, B. A., Adams, S. R. & Tsien, R. Y. (1998), *Science*, 281; 269-272.
22. Keppetipola, S. et al. (2003), *Focus*, 25.3; 7-11.
23. Spedding, G. in Ribosomes and Protein Synthesis (ed. Spedding, G.) 1-27 (Oxford University Press, New York, 1990).
24. Steinbacher, S. et al. (1994), *Science*, 265; 383-386.
25. Friguet, B., et al. (1985), *J Immunol Methods*, 77; 305-319.
26. Friguet, B., et al. (1989), *Res Immunol*, 140; 355-376.
27. Sunohara, T., et al. (2004), *J Biol Chem*, 279; 15368-15375.
28. Fuchs, A., et al. (1991), *Biochemistry*, 30; 6598-6604.
29. Mitraki, A., et al. (1991), *Science*, 253; 54-58.
30. King, J., et al. (1996), *Faseb J*, 10; 57-66.
31. Laemmli, U. K. (1970), *Nature*, 227; 680-685.
32. Steinbacher, S. et al. (1997), *J Mol Biol*, 267; 865-880.
33. Nakatogawa, H. & Ito, K. (2002), *Cell*, 108; 629-636 (2002).
34. Laemmli, U. K. (1970), *Nature*, 227; 680-685.
35. Friguet, B., et al. (1990), *J Biol Chem*, 265; 10347-10351.
36. Hanes, et al. (2002) *Proc. Natl. Acad. Sci. U.S.A.*, 99; 3440-3445.
37. Janzen, D. et al. (2002), *Molecular and Cellular Biology*, 22(24); 8562-8570.
38. Lovett, P., et al. (1996), *Microbiological Reviews*, 60(2): 366-385.
39. Morris, D., et al. (2000), *Molecular and Cellular Biology*, 20(23): 8635-8642.
40. Ominato, K., et al. (2002), *J. Biol. Chem.*, 277(39): 36380-36386.
41. Onouchi, H., et al. (2005), *Genes & Development*, 19:1799-1810.
42. U.S. Pat. No. 6,620,587—Taussig (2003).
43. Hayes, C. S., et al. (2002), *Proc. Natl. Acad. Sci.*, U.S.A., 99:3400-3405.
44. Speed, M. A., et al. (1997), *Protein Sci.*, 6:99-108.
45. Fang, P., et al. (2004), *Proc. Natl. Acad. Sci.*, 101 (12): 4059-4064.

What is claimed:

1. An isolated nascent molecule comprising a stall element having a sequence of a Formula I:

F-X1-WI-X2-GIRAGP            (SEQ ID NO:1), wherein at least one of X1 and X2 comprises 1 or more amino acid residues, and
where if X1 is STPV (SEQ ID NO: 2), then X2 is 1, 2, 3 or 4 histidine residues or HHHX, and
where if X2 is SQAQ (SEQ ID NO: 3), then X1 is 1, 2, 3 or 4 histidine residues or XHHH.

2. The isolated nascent molecule comprising the stall element of claim 1 wherein X1 is 1, 2, 3 or 4 histidine residues or XHHH, and X2 is SQAQ (SEQ ID NO:3).

3. The isolated nascent molecule comprising the stall element of claim 1 wherein X2 is 1, 2, 3 or 4 histidine residues or HHHX and X1 is STPV (SEQ ID NO: 2).

4. An isolated nascent molecule comprising a degradation tag and a stall element comprising a sequence of Formula I:
F-X1-WI-X2-GIRAGP (SEQ ID NO:1), wherein where if X1 is STPV (SEQ ID NO:2), then X2 is 1, 2, 3 or 4 histidine residues or HHHG or where if X2 is SQAQ (SEQ ID NO:3), then X1 is 1, 2, 3 or 4 histidine residues or XHHH.

5. The isolated nascent molecule comprising the stall element of claim 4 wherein the degradation tag sequence is 'ANDENYALAA' (SEQ ID NO:7).

6. A plasmid comprising:
a sequence encoding the nascent molecule comprising the stall element of claim 1.

7. The plasmid of claim 6 comprising one or more endonuclease restriction sites.

8. The plasmid of claim 6 comprising a C-terminal post stall element.

9. A composition enriched for transformed cells transformed with a plasmid comprising a sequence encoding a nascent molecule comprising an isolated stall element as defined in claim 1.

10. The composition of claim 9 wherein the transformed cells are E. coli cells.

11. The isolated nascent molecule comprising the stall element of claim 1 comprising a sequence of SEQ ID NO: 27.

12. The isolated nascent molecule comprising the stall element of claim 1 comprising a sequence of SEQ ID NO: 28.

13. An isolated nascent molecule comprising the stall element having a sequence:
F-Xaa Xaa Xaa Xaa-WI-SQAQ-GIRAGP (SEQ ID No. 25), wherein at least one Xaa is a histidine residue.

14. The isolated nascent molecule comprising the stall element of claim 1 further comprising an additional sequence encoding a nascent molecule.

15. The isolated nascent molecule comprising the stall element of claim 14 wherein the additional sequence is a peptide having a length of 1 to 900 amino acid residues.

16. An isolated nascent molecule comprising the stall element of a sequence:

F-HHHH-WI-Xaa-GIRAG          (SEQ ID NO: 29), wherein Xaa is a histidine residue.

17. An isolated nascent molecule comprising the stall element of a sequence:

F-Xaa-WI-HHHH-GIRAG          (SEQ ID NO: 30), wherein Xaa is a histidine residue.

* * * * *

SEQUENCE LISTING

```
<160> NUMBER OF SEQ ID NOS: 33

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Any amino acid
<220> FEATURE:
<221> NAME/KEY: MOD_RES
<222> LOCATION: (5)
<223> OTHER INFORMATION: Any amino acid
```

-continued

```
<220> FEATURE:
<223> OTHER INFORMATION: See specification as filed for detailed
      description of substitutions and preferred embodiments

<400> SEQUENCE: 1

Phe Xaa Trp Ile Xaa Gly Ile Arg Ala Gly Pro
 1               5                  10

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Thr Pro Val
 1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Gln Ala Gln
 1

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Any amino acid except His

<400> SEQUENCE: 4

Phe Xaa His His His Trp Ile His His His His Gly Ile Arg Ala Gly
 1               5                  10                  15

Pro

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: Any amino acid except His

<400> SEQUENCE: 5

Phe His His His His Trp Ile His His His Xaa Gly Ile Arg Ala Gly
 1               5                  10                  15

Pro

<210> SEQ ID NO 6
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Ile Arg Ala Gly Pro
 1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Asn Asp Glu Asn Tyr Ala Leu Ala Ala
 1               5                  10

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asn Cys Ser Asn Ile Gly Val Ala
 1               5

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Phe Ser Thr Pro Val Trp Ile Ser Gln Ala Gln Gly Ile Arg Ala Gly
 1               5                  10                  15

Pro

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Cys Pro Gly Cys Cys
 1               5

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 11
ttaagctgct aaagcgtagt tttcgtcgtt tgcg                                34

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggcgagctct tcagcacgcc cgtctgg                                        27

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggcctcgagc tgcgcaactg ttgggaagc                                      29

<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggcatccgtg ctggccctct cgagcaacgc ctcacctaac aa                       42

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gttgttaggt gaggcgttgc tcgagagggc cagcacggat gcc                      43

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 16

His His His His His His
  1               5

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 17

Arg Arg Asn Cys Ser Asn Ile Gly Val Ala Gln
  1               5                  10

<210> SEQ ID NO 18
<211> LENGTH: 22
<212> TYPE: PRT
<213> ORGANISM: Unknown
<220> FEATURE:
<223> OTHER INFORMATION: Description of Unknown: Sequence of
      mammalian virus origin

<400> SEQUENCE: 18

Met Gln Pro Leu Val Leu Ser Ala Lys Lys Leu Ser Ser Leu Leu Thr
  1               5                  10                  15

Cys Lys Tyr Ile Pro Pro
             20

<210> SEQ ID NO 19
<211> LENGTH: 25
<212> TYPE: PRT
<213> ORGANISM: Unknown
<220> FEATURE:
<223> OTHER INFORMATION: Description of Unknown: Sequence of
      fungi origin

<400> SEQUENCE: 19

Met Phe Ser Leu Ser Asn Ser Gln Tyr Thr Cys Gln Asp Tyr Ile Ser
  1               5                  10                  15

Asp His Ile Trp Lys Thr Ser Ser His
             20                  25

<210> SEQ ID NO 20
<211> LENGTH: 24
<212> TYPE: PRT
<213> ORGANISM: Unknown
<220> FEATURE:
<223> OTHER INFORMATION: Description of Unknown: Sequence of
      fungi origin

<400> SEQUENCE: 20

Met Asn Gly Arg Pro Ser Val Phe Thr Ser Gln Asp Tyr Leu Ser Asp
  1               5                  10                  15

His Leu Trp Arg Ala Leu Asn Ala
             20

<210> SEQ ID NO 21
<211> LENGTH: 13
<212> TYPE: PRT
<213> ORGANISM: Unknown
<220> FEATURE:
<223> OTHER INFORMATION: Description of Unknown: Sequence of
      plant origin

<400> SEQUENCE: 21

Ala Arg Arg Asn Cys Ser Asn Ile Gly Val Ala Gln Ile
  1               5                  10

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 22

Lys Asp Glu Leu
  1

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Any amino acid
<220> FEATURE:
<221> NAME/KEY: MOD_RES
<222> LOCATION: (4)
<223> OTHER INFORMATION: Any amino acid

<400> SEQUENCE: 23

Xaa Cys Ser Xaa Ile Gly Val Ala
  1               5

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(11)
<223> OTHER INFORMATION: region may encompass any amino acids other than
      the sequence 'Ser-Gln-Ala-Gln'

<400> SEQUENCE: 24

Phe Ser Thr Pro Val Trp Ile Xaa Xaa Xaa Xaa Gly Ile Arg Ala Gly
  1               5                  10                  15

Pro

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: region may encompass any amino acids other than
      the sequence 'Ser-Thr-Pro-Val'

<400> SEQUENCE: 25

Phe Xaa Xaa Xaa Xaa Trp Ile Ser Gln Ala Gln Gly Ile Arg Ala Gly
  1               5                  10                  15

Pro

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26
```

```
Phe His His His Trp Ile His His His Gly Ile Arg Ala Gly Pro
  1               5                  10                  15
```

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (8)..(10)
<223> OTHER INFORMATION: region may encompass 1-3 'His' residues

<400> SEQUENCE: 27

```
Phe His His His His Trp Ile His His His Gly Ile Arg Ala Gly Pro
  1               5                  10                  15
```

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(4)
<223> OTHER INFORMATION: region may encompass 1-3 'His' residues

<400> SEQUENCE: 28

```
Phe His His His Trp Ile His His His His Gly Ile Arg Ala Gly Pro
  1               5                  10                  15
```

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Any amino acid

<400> SEQUENCE: 29

```
Phe His His His His Trp Ile Xaa Gly Ile Arg Ala Gly Pro
  1               5                  10
```

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Any amino acid

<400> SEQUENCE: 30

```
Phe Xaa Trp Ile His His His His Gly Ile Arg Ala Gly Pro
  1               5                  10
```

<210> SEQ ID NO 31
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Phe His His His His Trp Ile His His His Gly Ile Arg Ala Gly
 1               5                  10                  15
Pro

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

His Cys Ser His Ile Gly Val Ala
 1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Any amino acid

<400> SEQUENCE: 33

Ala His Arg Arg Xaa Gln Ile His
 1               5
```